(12) United States Patent
Pushkarev et al.

(10) Patent No.: US 9,249,460 B2
(45) Date of Patent: Feb. 2, 2016

(54) METHODS FOR OBTAINING A SEQUENCE

(75) Inventors: Dmitry Pushkarev, Stanford, CA (US);
Stephen R. Quake, Stanford, CA (US);
Ayelet Voskoboynik, Aptos, CA (US);
Michael Kertesz, Menlo Park, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 0 days.

(21) Appl. No.: 13/608,778

(22) Filed: Sep. 10, 2012

(65) Prior Publication Data

US 2013/0079231 A1    Mar. 28, 2013

Related U.S. Application Data

(60) Provisional application No. 61/532,882, filed on Sep. 9, 2011.

(51) Int. Cl.
*C12Q 1/68* (2006.01)

(52) U.S. Cl.
CPC ............ *C12Q 1/6874* (2013.01); *C12Q 1/6806* (2013.01); *C12Q 1/6869* (2013.01)

(58) Field of Classification Search
CPC .. C12Q 1/6827; C12Q 1/6869; C12Q 1/6874; C40B 20/00; C40B 30/00
USPC .......................... 435/6.1, 6.11, 6.12; 506/7, 2
See application file for complete search history.

(56) References Cited

U.S. PATENT DOCUMENTS

| 5,614,389 A | 3/1997 | Auerbach |
| 5,733,733 A | 3/1998 | Auerbach |
| 5,849,558 A | 12/1998 | Morgan et al. |
| 5,888,737 A | 3/1999 | DuBridge et al. |
| 5,945,326 A | 8/1999 | Morgan et al. |
| 6,030,830 A | 2/2000 | Saxon et al. |
| 6,048,719 A | 4/2000 | Kong et al. |
| 6,048,731 A | 4/2000 | Kong et al. |
| 6,060,245 A | 5/2000 | Sorge et al. |
| 6,074,831 A | 6/2000 | Yakhini et al. |

(Continued)

FOREIGN PATENT DOCUMENTS

| EP | 0359714 B1 | 3/1990 |
| EP | 0869174 B1 | 10/1998 |

(Continued)

OTHER PUBLICATIONS

Cummings et al., "Combining target enrichment with barcode multiplexing for high throughput SNP discovery," BMC Genomics 2010, 11:641, published online Nov. 18, 2010.*

(Continued)

*Primary Examiner* — Samuel Woolwine
*Assistant Examiner* — Kaijiang Zhang
(74) *Attorney, Agent, or Firm* — Brown Rudnick LLP; Thomas C. Meyers

(57) ABSTRACT

The invention generally relates to methods for obtaining a sequence, such as a consensus sequence or a haplotype sequence. In certain embodiments, methods of the invention involve determining an amount of amplifiable nucleic acid present in a sample, partitioning the nucleic acid based upon results of the determining step such that each partitioned portion includes, on average, a subset of unique sequences, sequencing the nucleic acid to obtain sequence reads, and assembling a consensus sequence from the reads.

17 Claims, 7 Drawing Sheets

(56) References Cited

U.S. PATENT DOCUMENTS

| | | | |
|---|---|---|---|
| 6,162,400 | A | 12/2000 | Schembri |
| 6,191,267 | B1 | 2/2001 | Kong et al. |
| 6,245,545 | B1 | 6/2001 | Kong et al. |
| 6,313,284 | B1 | 11/2001 | Kwiatkowski et al. |
| 6,361,947 | B1 | 3/2002 | Dong et al. |
| 6,714,874 | B1 | 3/2004 | Myers et al. |
| 6,790,946 | B2 | 9/2004 | Kwiatkowski et al. |
| 6,846,658 | B1 | 1/2005 | Vaisvila et al. |
| 6,872,529 | B2 | 3/2005 | Su |
| 6,951,720 | B2 | 10/2005 | Burgin, Jr. et al. |
| 6,958,225 | B2 | 10/2005 | Dong |
| 7,244,567 | B2 | 7/2007 | Chen et al. |
| 7,247,486 | B2 | 7/2007 | Schembri |
| 7,406,385 | B2 | 7/2008 | Sorenson |
| 7,452,671 | B2 | 11/2008 | Shapero et al. |
| 7,575,865 | B2 | 8/2009 | Leamon et al. |
| 7,582,420 | B2 | 9/2009 | Oliphant et al. |
| 7,611,869 | B2 | 11/2009 | Fan |
| 7,709,197 | B2 † | 5/2010 | Drmanac |
| 7,901,891 | B2 | 3/2011 | Drmanac |
| 7,960,104 | B2 | 6/2011 | Drmanac et al. |
| 2002/0051994 | A1 | 5/2002 | Kwiatkowski et al. |
| 2002/0142314 | A1 | 10/2002 | Dong et al. |
| 2003/0008306 | A1 | 1/2003 | Turnbull et al. |
| 2003/0082535 | A1 | 5/2003 | Leushner et al. |
| 2003/0143599 | A1 | 7/2003 | Makarov et al. |
| 2003/0165841 | A1 | 9/2003 | Burgin et al. |
| 2003/0170652 | A1 | 9/2003 | Inoko et al. |
| 2003/0211506 | A1 | 11/2003 | Kong et al. |
| 2004/0002090 | A1 | 1/2004 | Mayer et al. |
| 2004/0067493 | A1 | 4/2004 | Matsuzaki et al. |
| 2004/0086892 | A1 | 5/2004 | Crothers et al. |
| 2004/0110153 | A1 | 6/2004 | Dong et al. |
| 2004/0171047 | A1 | 9/2004 | Dahl et al. |
| 2004/0191812 | A1 | 9/2004 | Davydova et al. |
| 2004/0209299 | A1 | 10/2004 | Pinter et al. |
| 2004/0224324 | A1 | 11/2004 | Dear |
| 2004/0248153 | A1 | 12/2004 | Dear et al. |
| 2005/0112636 | A1 | 5/2005 | Hurt et al. |
| 2005/0147973 | A1 | 7/2005 | Knott |
| 2005/0158769 | A1 | 7/2005 | Vaisvila et al. |
| 2006/0073493 | A1 | 4/2006 | Fasulo et al. |
| 2006/0281082 | A1 | 12/2006 | Zhu |
| 2007/0009894 | A1 | 1/2007 | Crothers |
| 2007/0099208 | A1 | 5/2007 | Drmanac et al. |
| 2007/0196849 | A1 | 8/2007 | Spier |
| 2008/0096255 | A1 | 4/2008 | Harbers et al. |
| 2008/0160511 | A1 | 7/2008 | Dawson et al. |
| 2008/0234136 | A1 | 9/2008 | Drmanac et al. |
| 2008/0274466 | A1 | 11/2008 | McKernan |
| 2009/0005252 | A1 | 1/2009 | Drmanac et al. |
| 2009/0011943 | A1 | 1/2009 | Drmanac et al. |
| 2009/0035823 | A1 | 2/2009 | Soldatov et al. |
| 2009/0099041 | A1 | 4/2009 | Church et al. |
| 2009/0105094 | A1 | 4/2009 | Heiner et al. |
| 2009/0118129 | A1 | 5/2009 | Turner |
| 2009/0118488 | A1 | 5/2009 | Drmanac et al. |
| 2009/0137404 | A1 | 5/2009 | Drmanac et al. |
| 2009/0137414 | A1 | 5/2009 | Drmanac et al. |
| 2009/0155781 | A1 | 6/2009 | Drmanac et al. |
| 2009/0176234 | A1 | 7/2009 | Drmanac et al. |
| 2009/0181861 | A1 | 7/2009 | Li et al. |
| 2009/0233291 | A1 | 9/2009 | Chen et al. |
| 2009/0264299 | A1 | 10/2009 | Drmanac et al. |
| 2009/0270273 | A1 | 10/2009 | Burns et al. |
| 2009/0298064 | A1 | 12/2009 | Batzoglou et al. |
| 2010/0028888 | A1 | 2/2010 | Smith et al. |
| 2010/0069263 | A1 | 3/2010 | Shendure et al. |
| 2010/0120098 | A1 † | 5/2010 | Grunenwald |
| 2011/0003701 | A1 | 1/2011 | Ferreri et al. |
| 2011/0015096 | A1 | 1/2011 | Chiu |
| 2011/0033854 | A1 † | 2/2011 | Drmanac |
| 2011/0071053 | A1 | 3/2011 | Drmanac et al. |
| 2011/0081687 | A1 | 4/2011 | McKernan |
| 2011/0159499 | A1 | 6/2011 | Hindson et al. |
| 2011/0201507 | A1 | 8/2011 | Rava et al. |
| 2011/0223585 | A1 | 9/2011 | Gullberg et al. |
| 2011/0251084 | A1 | 10/2011 | Brenan et al. |
| 2011/0281736 | A1 | 11/2011 | Drmanac et al. |
| 2011/0281738 | A1 | 11/2011 | Drmanac et al. |
| 2011/0319281 | A1 | 12/2011 | Drmanac |
| 2012/0011086 | A1 | 1/2012 | Zhang et al. |
| 2012/0135893 | A1 | 5/2012 | Drmanac et al. |

FOREIGN PATENT DOCUMENTS

| | | |
|---|---|---|
| EP | 0983288 B1 | 3/2000 |
| EP | 1048731 B1 | 11/2000 |
| EP | 1197549 B1 | 4/2002 |
| EP | 1303530 B1 | 4/2003 |
| EP | 1558764 B1 | 8/2005 |
| EP | 1598427 A1 | 11/2005 |
| EP | 1616008 B1 | 1/2006 |
| EP | 1757683 A1 | 2/2007 |
| EP | 969102 B1 | 12/2007 |
| EP | 2058396 A1 | 5/2009 |
| EP | 2202322 A1 | 6/2010 |
| EP | 2620497 A1 | 7/2013 |
| WO | WO-96/23904 A1 | 8/1996 |
| WO | WO-98/07738 A1 | 2/1998 |
| WO | WO-98/51698 A1 | 11/1998 |
| WO | WO-98/51783 A1 | 11/1998 |
| WO | WO-99/13094 A2 | 3/1999 |
| WO | WO-01/94544 A2 | 12/2001 |
| WO | WO-02/090522 A2 | 11/2002 |
| WO | WO-02/103046 A2 | 12/2002 |
| WO | WO-03/036434 A2 | 5/2003 |
| WO | WO-03/083137 A2 | 10/2003 |
| WO | 2004022758 A1 | 3/2004 |
| WO | WO-2004/044549 A2 | 5/2004 |
| WO | WO-2004/058989 A2 | 7/2004 |
| WO | WO-2004/059289 A2 | 7/2004 |
| WO | WO-2004/092375 A2 | 10/2004 |
| WO | WO-2005/021717 A2 | 3/2005 |
| WO | WO-2005/030929 A2 | 4/2005 |
| WO | WO-2006/003721 A1 | 1/2006 |
| WO | 2006119066 A2 | 11/2006 |
| WO | 2006137734 A1 | 12/2006 |
| WO | WO-2006/138257 A2 | 12/2006 |
| WO | WO-2006/138284 A2 | 12/2006 |
| WO | WO-2007/024653 A2 | 3/2007 |
| WO | WO-2007/044245 A2 | 4/2007 |
| WO | 2007/073171 A2 | 6/2007 |
| WO | WO-2007/092538 A2 | 8/2007 |
| WO | WO-2007/101075 A2 | 9/2007 |
| WO | WO-2007/133831 A2 | 11/2007 |
| WO | WO-2008/083327 A2 | 7/2008 |
| WO | WO-2008/084405 A2 | 7/2008 |
| WO | 2009045344 A2 | 4/2009 |
| WO | WO-2009/076238 A2 | 6/2009 |
| WO | WO-2009/089384 A1 | 7/2009 |
| WO | WO-2009/120183 A2 | 10/2009 |
| WO | WO-2009/132028 A1 | 10/2009 |
| WO | 2010148039 A2 | 12/2010 |
| WO | 2011/053987 A1 | 5/2011 |
| WO | WO-2011/066476 A1 | 6/2011 |
| WO | WO-2012/005595 A2 | 1/2012 |
| WO | WO-2012/008831 A1 | 1/2012 |
| WO | 2012029577 A1 | 3/2012 |
| WO | 2012080591 A1 | 6/2012 |
| WO | 2012142611 A2 | 10/2012 |
| WO | 2012149042 A2 | 11/2012 |
| WO | 2012162267 A2 | 11/2012 |
| WO | 2013036929 A1 | 3/2013 |

OTHER PUBLICATIONS

Farias-Hesson et al., "Semi-Automated Library Preparation for High-Throughput DNA Sequencing Platforms," J. Biomed. Biotechnol., 2010:617469, published online Jun. 8, 2010.*

Xu et al., "Dual primer emulsion PCR for next generation DNA sequencing," BioTechniques 2010, 48:409-412.*

International Search Report and Written Opinion for PCT/US12/54461, dated Feb. 4, 2013, 19 pages.

(56) References Cited

OTHER PUBLICATIONS

Browning, et al. Rapid and Accurate Haplotype Phasing and Missing-Data Inference for Whole-Genome Association Studies by Use of Localized Haplotype Clustering. Am J Hum Genet. Nov. 2007;81(5):1084-97. Epub Sep. 21, 2007.
Dear, et al. Happy Mapping, Practical Approach Series. vol. 184, 1997, pp. 95-123.
Howie, et al. A Flexible and Accurate Genotype Imputation Method for the Next Generation of Genome-Wide Association Studies. PLoS Genet. Jun. 2009;5(6):e1000529. Epub Jun. 19, 2009.
Huang, et al. CAP3: A DNA Sequence Assembly Program. Genome Res. Sep. 1999;9(9):868-77.
Kitzman, et al. Haplotype-resolved genome sequencing of a Gujarati Indian individual. Nat Biotechnol. Jan. 2011;29(1):59-63. Epub Dec. 19, 2010.
Peters, et al. Accurate whole-genome sequencing and haplotyping from 10 to 20 human cells. Nature. Jul. 11, 2012;487(7406):190-5. doi: 10.1038/nature11236.
Third-Party Observations in Relation to GB Application 1216076.8, May 23, 2014, 7 pages.
Lasken, et al., "Mechanism of chimera formation during the Multiple Displacement Amplification reaction," BMC Biotechnology 2007, 7:19, 11 pages.
Arneson, et al., "PCR-based whole genome amplification," 2007, Chapter 18 (pp. 293-317) of Hughes, S. and Moody, A., PCR (Method Express), Scion Publishing Ltd, Oxfordshire UK.
Chen et al., "Scanning the human genome at kilobase resolution," Genome Research (2008); vol. 18, pp. 751-762, See Abstract, p. 752 col. 1 para 2, Fig 1. Available at http://genome.cshlp.org/content/18/5/751.full.pdf+html.
Combined Search and Examination Report under Section 17 & 18(3) for Application No. GB1216076.8, dated Feb. 25, 2013, 9 pages.
Examination Report under Section 18(3) for Application No. GB1216076.8, dated Feb. 26, 2014, 5 pages.
Further Search Report under Section 17 for Application No. GB1216076.8, dated Feb. 23, 2014, 2 pages.
Grothues et al., 1993, "PCR amplification of megabase DNA with tagged random primers (T-PCR)" Nucleic Acids Research 21:1321-1322.
Kapa Library Quantification Press Release (Jul. 1, 2010) available at: www.anachem.co.uk/news/2010/kapangs <http://www.anachem.co.uk/news/2010/kapangs> The Internet Archive Wayback Machine shows at: http://web.archive.org/web//http://www.anachem.co.uk/news/2010/kapangs and http://web.archive.org/web/20101108005835/http://www.anachem.co.uk/news/2010/kapangs <http://web.archive.org/web//http://www.anachem.co.uk/news/2010/kapangs%20and%20http://web.archive.org/web/20101108005835/http://www.anachem.co.uk/news/2010/kapangs> that this.
Third-Party Observations in Relation to GB Application 1216076.8, Sep. 12, 2013, 6 pages.
Salazar-Gonzalez et al., "Deciphering human immunodeficiency virus . . . ", Journal of Virology (2008); vol. 82, pp. 3952-3970, See whole document, esp. p. 3954 col. 2 para 2—p. 3955 col. 1 para 4. Available at http://jvi.asm.org/content/82/8/3952.full.pdf+html.
Supplement Third-Party Observations in Relation to GB Application 1216076.8, Nov. 1, 2013, 14 pages.
Syed, et al., "Optimized library preparation method for next-generation sequencing," 2009, Nature Methods 6 (Oct. 2009), pp. i-ii.
Third-Party Submission Under 37 CFR 1.290 Concise Description of Relevance with Pre-Issuance Submission Under 37 C.F.R. 1.290 filed in U.S. Appl. No. 13/608,778 on Sep. 24, 2013 (39 pages).
Voskoboynik et al., "The genome sequence of the colonial chordate, Botryllus schlosseri," eLife 2013; 2:e00569, 24 pages.
Supplementary European Search Report issued for 12830052.2, mailed on May 7, 2015.
Emily H. Turner, et al. "Methods for Genomic Partitioning", Annual Review of Genomics and Human Genetics, vol. 10, No. 1, (Sep. 1, 2009), pp. 263-284.
G. Bentley et al., "High-Resolution, high-throughput HLA genotyping by next-generation sequencing", Tissue Antigens, vol. 74, No. 5., (Nov. 1, 2009), pp. 393-403.
Examination Report dated Oct. 1, 2015, for UK Patent Application No. GB1216076.8, filed Oct. 9, 2012 (14 pages).
Arneson et al., "PCR-based whole genome amplification", 2007, Chapter 18 (pp. 293-317) of Hughes, S. and Moody, A., PCR (Method Express), Scion Publishing Ltd, Oxfordshire UK.†
Jiang, et al., "Old can be new again: Happy whole genome sequencing, mapping and assembly," Apr. 15, 2009, Int'l J. Bio. Sci. 5:298-303.†
Syed et al., "Optimized library preparation method for next-generation sequencing," 2009, Nature Methods 6 (Oct. 2009), pp. i-ii.†

\* cited by examiner
† cited by third party

USING PCR

1. Ligate A-prim-A

2. Circularize

Final product:

USING RESTRICTION ENZYMES

1. Ligate A-rest-A

2. Circularize  3. Cut with restriction enzyme

Final product:

SEQUENCE LISTING

<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 1
ccatctcatc cctgcgtgtc tccgactcag        30

<210> SEQ ID NO 2
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 2
tctccgactc ag        12

```
<210> SEQ ID NO 3
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 3
cctatcccct gtgtgccttg gcagtctcag                                    30

<210> SEQ ID NO 4
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 4
tggcagtctc ag                                                       12

<210> SEQ ID NO 5
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 5
ccatctcatc cctgcgtgtc tccg                                          24

<210> SEQ ID NO 6
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 6
cctatcccct gtgtgccttg gcagt                                         25
```

METHODS FOR OBTAINING A SEQUENCE

RELATED APPLICATION

The present application claims the benefit of and priority to U.S. provisional patent application Ser. No. 61/532,882, filed Sep. 9, 2011, the content of which is incorporated by reference herein in its entirety.

GOVERNMENT SUPPORT

This invention was made with Government support under Grant Number AG037968 awarded by the National Institute of Health (NIH). The Government has certain rights in this invention.

FIELD OF THE INVENTION

The invention generally relates to methods for obtaining a sequence, such as a consensus sequence or a haplotype sequence.

BACKGROUND

Methods to sequence or identify significant segments of the human genome and genetic variations within those segments are becoming commonplace. However, a major impediment to understanding the health implications of genomic variation lies in the ability to correlate genomic differences with the human health consequences of those differences. Whole genome sequencing is an important first step toward elucidation of the genomic underpinnings of human health. Once sequenced, genomic DNA must be assembled or aligned to a reference sequence. A generally-accepted protocol for genome assembly involves using fosmids and BAC libraries in which long pieces of DNA are introduced into bacterial cells that are sequenced independently and reassembled. Such a process is expensive, laborious, and time consuming (e.g., a few weeks to months).

Recent advances in sequencing throughput and library preparation has allowed mammalian-sized genomes to be sequenced in a matter of days. Current sequencing technologies allow the generation of enormous amounts of sequence using short sequence reads (i.e., lengths of about 100 bp to about 200 bp). Those technologies provide up to 30 GB of sequences per lane, which is equivalent to 10× coverage of the human genome.

However, application of those technologies to de-novo genome assemblies is limited by short sequence read length, which is insufficient to resolve complex genome structure and to produce consistent genome assembly. Further, short sequence reads cannot be used to obtain phasing data (i.e., which variants are on the same chromosome). Additionally, assembly from short reads requires construction of a de-bruign graph, which is a computationally-intensive process requiring supercomputers with large amount of RAM, which limits application to large sequencing centers with access to supercomputers. Thus, it is difficult and expensive to use short sequence reads to get quality de-novo reference genome assemblies.

SUMMARY

The invention generally relates to methods for obtaining a sequence, such as a consensus sequence or a haplotype sequence. Methods of the invention allow for sequencing of long continuous (kilobase scale) nucleic acid fragments using conventional short read sequencing technologies. Methods of the invention are accomplished by determining an amount of amplifiable nucleic acid present in a sample, partitioning the nucleic acid based upon results of the determining step such that each partitioned portion includes, on average, a subset of unique sequences, sequencing the nucleic acid to obtain sequence reads, and assembling a consensus sequence from the reads. Limiting the number of amplifiable molecules per partitioned portion greatly reduces or eliminates chances of having a repeated or homologous sequence within a partitioned portion. Thus, sample complexity is significantly reduced, which reduces ambiguity in the reconstruction of a consensus sequence. In some cases, the reconstruction can achieve complete unambiguity. In this manner, methods of the invention allow conversion of short sequence reads (about 100 bp to about 200 bp) into intermediate sized fragments (10,000 bp) that can be assembled into full chromosomes to provide reference quality assemblies.

Nucleic acid obtained from biological samples typically is fragmented to produce suitable fragments for analysis. Thus, methods of the invention may further involving an initial step of fragmenting obtained nucleic acid. To further provide for unambiguous reconstruction of a consensus sequence, methods of the invention may also involve attaching unique marker identifiers to ends of each fragment, thus ensuring that homologous fragments, for example originating from homologous copies of chromosomes, can be detected based upon the unique markers that are attached to each fragment. In certain embodiments, the unique markers are bar code sequences. In some embodiments, the labels are adaptor primer sequences. These adaptor sequences described in the invention, in some embodiments, allow resolving assembly ambiguities by linking the related sequence information of sequence segments together. The adaptor sequences adjacent to the ends of the one or more nucleic acids can be the same or different. In other embodiments, to further provide for unambiguous reconstruction of a consensus sequence, methods of the invention may also involve attaching labels to the nucleic acids in each partitioned portion. Exemplary labels include nucleic acid binding proteins, optical labels, nucleotide analogs, and others known in the art.

Partitioning of the fragments into partitioned portions may be by any method known in the art. For example, partitioning may involve dispensing the sample into different wells of a microwell plate, or partitioning may involve segmenting the sample into droplets. In particular embodiments, partitioning is performed under microfluidic control.

After partitioning, the fragmented nucleic acids may be amplified by any methods known in the art. In particular embodiments, PCR is used to amplify the fragments. The amplified fragments in each partitioned portion may then be fragmented and bar code sequences are attached to these fragments. Fragmenting may be by any method known in the art, such as restriction digesting or by application of mechanical force, e.g., sonication.

After bar codes have been incorporated into the nucleic acid templates, the templates are sequenced. Sequencing may be by any method known in the art. In certain embodiments, sequencing is sequencing by synthesis. In other embodiments, sequencing is single molecule sequencing by synthesis. In certain embodiments, sequencing involves hybridizing a primer to the template to form a template/primer duplex, contacting the duplex with a polymerase enzyme in the presence of a detectably labeled nucleotides under conditions that permit the polymerase to add nucleotides to the primer in a template-dependent manner, detecting a signal from the incorporated labeled nucleotide, and sequentially repeating the contacting and detecting steps at least once, wherein sequential detection of incorporated labeled nucleotide determines the sequence of the nucleic acid. Exemplary detectable labels include radiolabels, florescent labels, enzymatic labels, etc. In particular embodiments, the detectable label may be an optically detectable label, such as a fluorescent label. Exemplary fluorescent labels include cyanine, rhodamine, fluorescien, coumarin, BODIPY, alexa, or conjugated multi-dyes.

Another aspect of the invention provides methods for assembling a consensus sequence that involve obtaining nucleic acid, fragmenting the nucleic acid, determining an amount of amplifiable nucleic acid present in a sample, partitioning the fragmented nucleic acids based upon results of the determining step, amplifying the partitioned nucleic acids, attaching bar codes to the amplified nucleic acid, sequencing the nucleic acid to obtain bar coded sequence reads, and assembling a consensus sequence from the reads. In certain embodiments, each partitioned portion includes, on average, a unique subset of nucleic acids.

Methods of the invention also provide for determining an amount of amplifiable nucleic acid in a sample, in which each amplifiable nucleic acid includes a target nucleic acid coupled to at least one known sequence. In one embodiment, the at least one sequence is adaptor sequence that includes a primer sequence. The at least one known sequence can also include a unique tag, such as a barcode sequence. The amplifiable nucleic acid can have the known sequences coupled to both ends so that the nucleic acids are exponentially amplified. The amount of amplifiable nucleic acids can be determined with, for example, digital PCR or qPCR. After determining the amount of amplifiable nucleic acids, the amplifiable nucleic acids can be partitioned based on the determining step, such that each partition, on average, contains a unique subset of sequences. Once partitioned, the partitioned nucleic acids can be amplified such that nucleic acids with known sequences on both ends are exponentially amplified. The partitioned nucleic acids can be sequenced to obtain sequence reads and a sequence can be obtained from the reads.

BRIEF DESCRIPTION OF THE DRAWINGS

FIG. 5A shows a method that uses PCR and FIG. 5B shows a method that uses a restriction enzyme.

DETAILED DESCRIPTION

Methods of the invention provide a highly-scalable library construction method that allows accurate reconstruction of intermediate sized genomic fragments from short paired reads. According to embodiments of the invention, genomic DNA is converted into a library of intermediately sized fragments 8-10 kb that are amplified inside partitioned portions after artificially limiting number of template molecules per portion. Resulting amplicon libraries are fragmented and converted to sequencing libraries labeled with unique bar codes to allow reads to be split according to partitioned portion after sequencing. Long fragments are then reassembled using a sequencing algorithm from the short paired reads.

Figure 1:
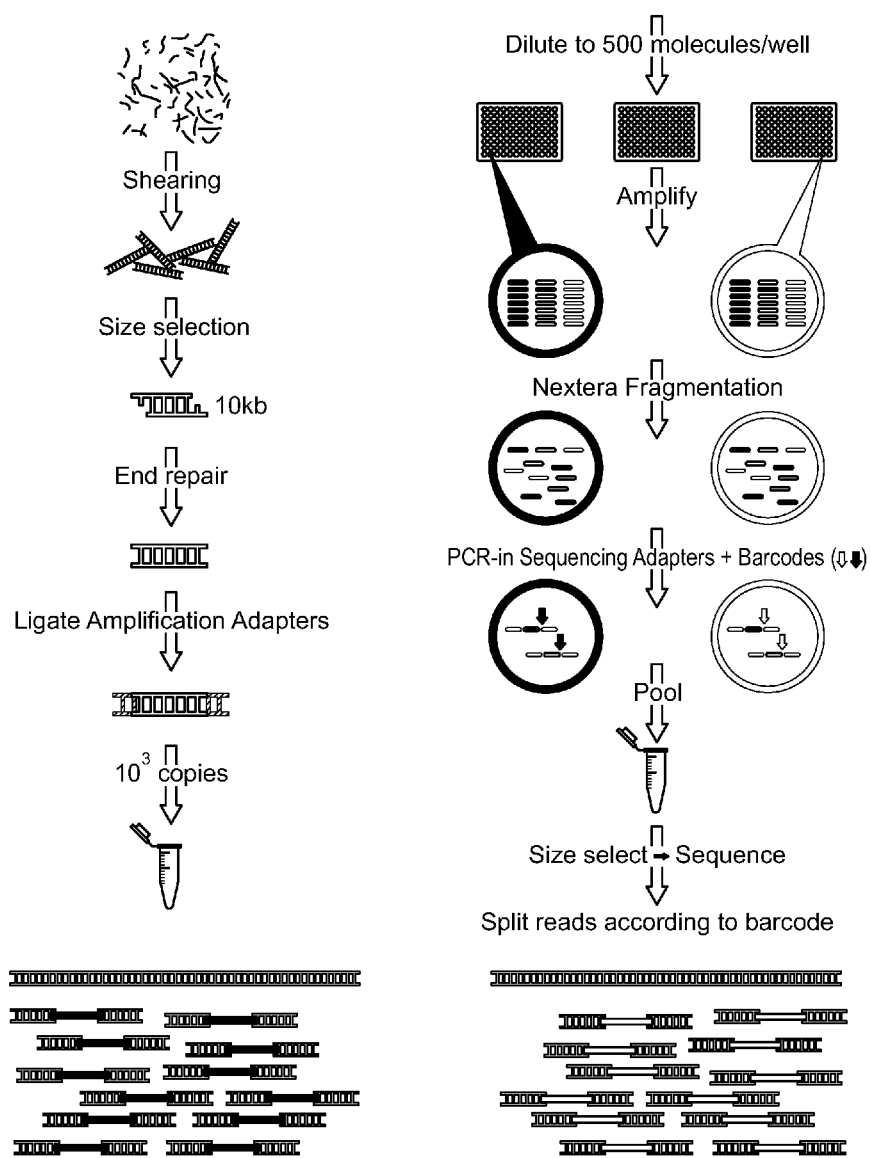
FIG. 1 is a diagram showing an exemplary embodiments of methods of the invention.

FIG. 1 provides an exemplary embodiment of methods of the invention. In one embodiment, nucleic acid template molecules (e.g., DNA or RNA) are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. Biological samples for use in the present invention include viral particles or preparations. Nucleic acid template molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid template molecules can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA. A sample may also be isolated DNA from a non-cellular origin, e.g. amplified/isolated DNA from the freezer.

Nucleic acid template molecules can be obtained as described in U.S. Patent Application Publication Number US2002/0190663 A1, published Oct. 9, 2003. Generally, nucleic acid can be extracted from a biological sample by a variety of techniques such as those described by Maniatis, et al., Molecular Cloning: A Laboratory Manual, Cold Spring Harbor, N.Y., pp. 280-281 (1982).

Nucleic acid obtained from biological samples typically is fragmented to produce suitable fragments for analysis. Template nucleic acids may be fragmented or sheared to desired length, using a variety of mechanical, chemical and/or enzymatic methods. DNA may be randomly sheared via sonication, e.g. Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In one embodiment, nucleic acid from a biological sample is fragmented by sonication. In another embodiment, nucleic acid is fragmented by a hydroshear instrument. Generally, individual nucleic acid template molecules can be from about 2 kb bases to about 40 kb. In a particular embodiment, nucleic acids are about 6 kb-10 kb fragments. Nucleic acid molecules may be single-stranded, double-stranded, or double-stranded with single-stranded regions (for example, stem- and loop-structures).

A biological sample as described herein may be homogenized or fractionated in the presence of a detergent or surfactant. The concentration of the detergent in the buffer may be about 0.05% to about 10.0%. The concentration of the detergent can be up to an amount where the detergent remains soluble in the solution. In one embodiment, the concentration of the detergent is between 0.1% to about 2%. The detergent, particularly a mild one that is nondenaturing, can act to solubilize the sample. Detergents may be ionic or nonionic. Examples of nonionic detergents include triton, such as the Triton® X series (Triton® X-100 t-Oct-$C_6H_4$—($OCH_2$—$CH_2)_x$OH, x=9-10, Triton® X-100R, Triton® X-114 x=7-8), octyl glucoside, polyoxyethylene(9)dodecyl ether, digitonin, IGEPAL® CA630 octylphenyl polyethylene glycol, n-octyl-beta-D-glucopyranoside (betaOG), n-dodecyl-beta, Tween® 20 polyethylene glycol sorbitan monolaurate, Tween® 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14EO6), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulf-onate. It is contemplated also that urea may be added with or without another detergent or surfactant.

Lysis or homogenization solutions may further contain other agents, such as reducing agents. Examples of such reducing agents include dithiothreitol (DTT), .beta.-mercaptoethanol, DTE, GSH, cysteine, cysteamine, tricarboxyethyl phosphine (TCEP), or salts of sulfurous acid.

Size selection of the nucleic acids may be performed to remove very short fragments or very long fragments. The nucleic acid fragments can be partitioned into fractions comprising a desired number of fragments using any suitable method known in the art. In some embodiments, the fractions include about 1, 2, 5, 10, 50, 100, 250, 500, 750, 1000, 1500, 2000, 5000 or 10,000 molecules. Suitable methods to limit the fragment size in each fragment are known in the art. In various embodiments of the invention, the fragment size is limited to 1, 2, 3, 4, 5, 7, 10, 12, 15, 20, 25, 30, 50, 100 kb or longer.

In various embodiments, the fragments are amplified after partitioning. Any amplification method known in the art may be used. Examples of amplification techniques that can be used include, but are not limited to, quantitative PCR, quantitative fluorescent PCR (QF-PCR), multiplex fluorescent PCR (MF-PCR), real time PCR (RTPCR), single cell PCR, restriction fragment length polymorphism PCR (PCR-RFLP), PCK-RFLPIRT-PCR-IRFLP, hot start PCR, nested PCR, in situ polonony PCR, in situ rolling circle amplification (RCA), bridge PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938.

In some embodiments, end repair is performed to generate blunt end 5' phosphorylated nucleic acid ends using commercial kits, such as those available from Epicentre Biotechnologies (Madison, Wis.).

Amplification adapters may be attached to the fragmented nucleic acid. Amplification adapters may be attached prior or subsequent to partitioning the nucleic acid. Adapters may be commercially obtained, such as from Integrated DNA Technologies (Coralville, Iowa). In certain embodiments, the adapter sequences are attached to the template nucleic acid molecule with an enzyme. The enzyme may be a ligase or a polymerase. The ligase may be any enzyme capable of ligating an oligonucleotide (RNA or DNA) to the template nucleic acid molecule. Suitable ligases include T4 DNA ligase and T4 RNA ligase (such ligases are available commercially, from New England Biolabs). Methods for using ligases are well known in the art. Alternatively, amplification adapters can be added to the target polynucleotide of interest via an intermediate polynucleotide that is comprised of two or more amplification adapters.

Adapters can contain one or more of a variety of sequence elements, including but not limited to, one or more amplification primer annealing sequences or complements thereof, one or more sequencing primer annealing sequences or complements thereof, one or more barcode sequences, one or more common sequences shared among multiple different adapters or subsets of different adapters, one or more restriction enzyme recognition sites, one or more overhangs complementary to one or more target polynucleotide overhangs, one or more probe binding sites (e.g. for attachment to a sequencing platform, such as a flow cell for massive parallel sequencing, such as developed by Illumina, Inc.), one or more random or near-random sequences (e.g. one or more nucleotides selected at random from a set of two or more different nucleotides at one or more positions, with each of the different nucleotides selected at one or more positions represented in a pool of adapters comprising the random sequence), and combinations thereof. Two or more sequence elements can be non-adjacent to one another (e.g. separated by one or more nucleotides), adjacent to one another, partially overlapping, or completely overlapping. For example, an amplification primer annealing sequence can also serve as a sequencing primer annealing sequence. Sequence elements can be located at or near the 3' end, at or near the 5' end, or in the interior of the adapter oligonucleotide. When an adapter oligonucleotide is capable of forming secondary structure, such as a hairpin, sequence elements can be located partially or completely outside the secondary structure, partially or completely inside the secondary structure, or in between sequences participating in the secondary structure. For example, when an adapter oligonucleotide comprises a hairpin structure, sequence elements can be located partially or completely inside or outside the hybridizable sequences (the "stem"), including in the sequence between the hybridizable sequences (the "loop"). In some embodiments, the first adapter oligonucleotides in a plurality of first adapter oligonucleotides having different barcode sequences comprise a sequence element common among all first adapter oligonucleotides in the plurality. In some embodiments, all second adapter oligonucleotides comprise a sequence element common among all second adapter oligonucleotides that is different from the common sequence element shared by the first adapter oligonucleotides. A difference in sequence elements can be any such that at least a portion of different adapters do not completely align, for example, due to changes in sequence length, deletion or insertion of one or more nucleotides, or a change in the nucleotide composition at one or more nucleotide positions (such as a base change or base modification). In some embodiments, an adapter oligonucleotide comprises a 5' overhang, a 3' overhang, or both that is complementary to one or more target polynucleotides. Complementary overhangs can be one or more nucleotides in length, including but not limited to 1, 2, 3, 4, 5, 6, 7, 8, 9, 10, 11, 12, 13, 14, 15, or more nucleotides in length. Complementary overhangs may comprise a fixed sequence. Complementary overhangs may comprise a random sequence of one or more nucleotides, such that one or more nucleotides are selected at random from a set of two or more different nucleotides at one or more positions, with each of the different nucleotides selected at one or more positions represented in a pool of adapters with complementary overhangs comprising the random sequence. In some embodiments, an adapter overhang is complementary to a target polynucleotide overhang produced by restriction endonuclease digestion. In some embodiments, an adapter overhang consists of an adenine or a thymine.

Figure 6:
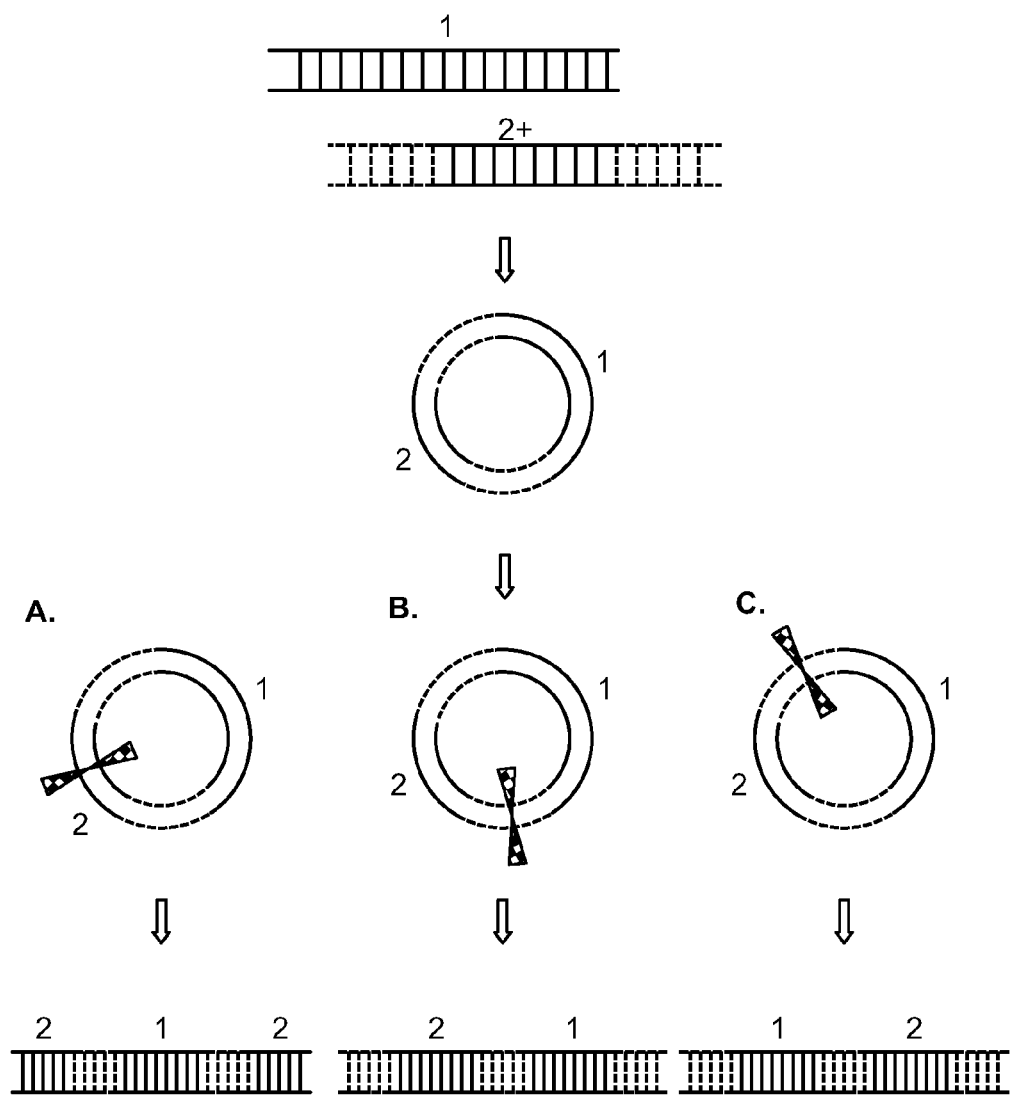
FIG. 6 demonstrates an example of attaching adapters to target polynucleotide according to some embodiments of the invention.

The adapters can be added by ligating a target polynucleotide to an intermediate polynucleotide comprised of compatible adapter ends. The compatible adapter ends can be kept under ligation conditions usually including a ligase, which facilitates the nucleic acid ends to intermolecularly ligate, thereby producing a circularized nucleic acid molecule. In some embodiments, the intermediate polynucleotide comprises a cleavable adapter thereby allowing the transformation of the circular polynucleotide into a linearized molecule with adapters located at each end (FIG. 6 A, B, C). The cleavable adapter may comprise a restriction endonuclease recognition site specific for a restriction endonuclease. The intermediate polynucleotide may comprise a cleavable adapter, for example a nicked adapter. For another example, the adaptor may comprise a cleavable adapter. The cleavable site in the adapter may be a deoxyuridine nucleotide which can be cleaved by uracil DNA glycosylase (UDG) and an AP-lyase. The cleavable adapter may comprise a 3' phosphorothiolate linkage cleaved by a metal ion, included but not limited to $Ag^+$, $Hg^{2+}$ or $Cu^{2+}$. The cleavage reaction may be at a pH of at least about 5 to 9. The temperature for the cleavage reaction may be selected at a temperature of about 22° to 37° degrees Celsius.

There are several ligation methods that can be employed to attach the adapters to a target polynucleotide. Ligation methods can include directional cloning, which uses "sticky ends". Sticky can be are generated by treating a polynucleotide with restriction enzymes to create complementary over-hanging ends. In the presence of a ligase complementary over-hanging ends may be ligated together. Ligation can be performed using non-directional cloning methods by the use of "blunt ends". In certain embodiments, following fragmentation, the ends of the fragments may be repaired, trimmed (e.g. using an exonuclease), or filled (e.g., using a polymerase and dNTPs), to form blunt ends. The blunt ends may have phosphates at the 5' ends and a hydroxyl at each 3' end of the target polynucleotide and the intermediate polynucleotide; alternatively, one or more 5' ends may lack a 5' phosphate. In the presence of a ligase enzyme, the blunt ends phosphates at the 5' ends and hydroxyl at the 3' ends may be ligated together. In certain embodiments, single strand overhangs can be removed to form blunt ends by the use of particular exonucleases that cut free single strand nucleic acids but do not cut double strand nucleic acids. Examples of such exonucleases include, but are not limited to: Exo VII, Exonuclease I, Exonuclease T, Lambda Exonuclease, and T7 Exonuclease.

Alternatively, one could ligate the target polynucleotide and the intermediate polynucleotide using T-A end cloning method. T-A cloning is a subcloning technique that does not use restriction enzymes generated sticky ends. Upon generating blunt ends, the ends can be treated with a polymerase and dATP to form a template independent addition to the 3'-end and the 5'-end of the fragments, thus producing a single A overhanging. The T-A cloning technique relies on the ability of adenine (A) and thymine (T) to complementary base pair on different DNA fragments to hybridize and, in the presence of ligase to form a circular polynucleotide. Alternatively, an investigator can use PCR generated fragments that already contain an "A" overhang by employing a DNA polymerase that leaves an adenine "A" nucleotide at the 3'end during amplification, such as Taq DNA polymerase or equivalents. Thermostable polymerases containing extensive 3' to 5' exonuclease activity are not suitable for this purpose, as they do not leave the 3' adenine-overhangs. The probability probability of Taq DNA polymerase adding the terminal adenosine overhang may be increased by using PCR primers that have guanines at the 5' end. In another example, thymines (T) can be added using a dideoxythymidine triphosphate (ddTTP) and a terminal transferase. This tailing leaves the vector with a single 3'-overhanging thymine residue on each blunt end. Similarly, one could use G-C cloning in the presence of ligase to form a circular polynucleotide. Commercialized kits with pre-prepared reagents and terminal transferases are available T-A or G-C cloning and well known in the art. T-A/G-C cloning are best utilized when directional cloning is not a requirement.

According to one method the target polynucleotide can be ligated by PCR to the intermediate polynucleotide, by generating a circularized form using a topoisomerase using an intermediate ploynucleotide with adapters. In some embodiments, the adapters containa 5'-(C/T)CCTT-3' recognition site at the 3' ends. The intermediate polynucleotide may contain a topoisomerase enzyme covalently attached to the recognition site generating an intermediate polynucleotide-TOPO modified molecule. The intermediate-TOPO polynucleotide may be mixed with target polynucleotides generated by PCR, allowing for recognition of the intermediate polynucleotide-TOPO 3' by the 5' ends. The strands may be covalently linked by the topoisomerase to form a circular polynucleotide.

In some applications, amplification adapters are added to a target polynucleotide. The target polynucleotide can be single or double stranded. accordingly, the adapters can be either single stranded or double stranded depending on whether the target polynucleotide employed is single or double stranded. A single strand target template may originate from RNA or DNA. CircLigase™ II is a thermostable ssDNA ligase that catalyzes intramolecular ligation of ssDNA templates having a 5'-phosphate and a 3'-hydroxyl group (Epicentre). The target polynucleotide can be further obtained from fragmentation of large DNA or RNA molecules, PCR amplification or from cloned vectors containing the target sequence of interest, such as a commercial cloned gene expression libraries of RNA or DNA.

Figure 5A:
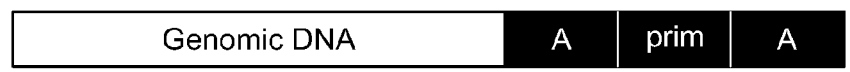
FIGS. 5A-B are schematics showing that end markers can be attached by circularizing long fragments and using a pool of circularization adapters that contain matched pairs of known sequences that are ligated to opposite ends of long fragments.
Figure 5A:
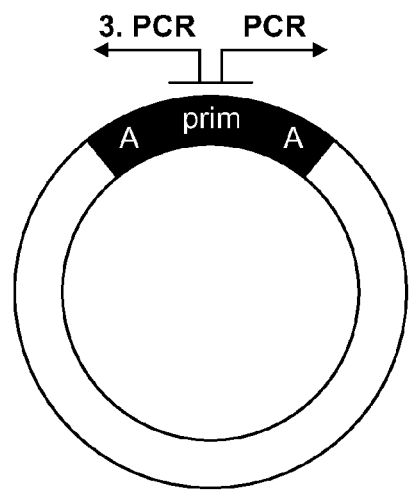
Figure 5A:
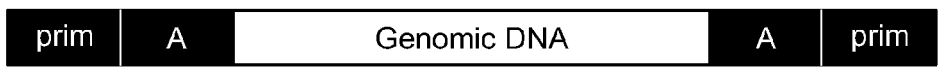
Figure 5B:
Figure 5B:
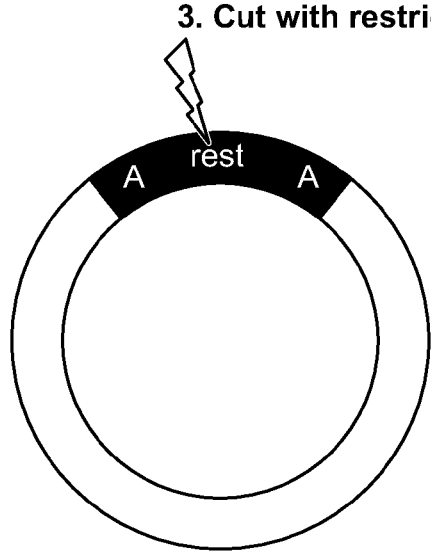
Figure 5B:

In some embodiments of the invention, end markers/adapters can be attached by circularizing long fragments and using a pool of circularization adapters that contain matched pairs of known sequences that are ligated to opposite ends of long fragments. Such paired adapters may be attached to long fragments allowing for validation of long fragment assembly, for example by checking whether a correctly matching pair of adapters is found on opposite ends of a reconstructed fragment (FIGS. 5A-B).

The ratio of the target polynucleotide and the intermediate polynucleotide within the circular polynucleotide may be varied. In such cases, reiterative steps described above may be performed using multiple cloning site identification elements or nicked identification elements contained within the adapters. Accordingly, a circular polynucleotide containing more than a 1:1 target polynucleotide: intermediate polynucleotide ratio may be generated. In some embodiments, target polynucleotide and the intermediate polynucleotide are present at a 1:2, 1:3, 1:4, 1:6, 1:8, 1:10 or 1:20 ratio.

Adapters containing particular identification elements may be used and may be useful in downstream analysis of the target polynucleotide. More specifically, one could use adapters that contain a unique tag identification element. Tags can include, but are not limited to, for example, a fluorophore, a quantum dot, a dendrimer, a nanowire, a bead, a peptide, a protein, a magnetic bead, a methyl group, a methyltransferase, a non-cutting restriction enzyme, a zinc-finger protein, an antibody, a transcription factor, a DNA binding protein, a hairpin polyamide, a triplex-forming oligodeoxynucleotide, a peptide nucleic acid, a nucleic acid or the equivalents thereof. The methods may include the use of two or more different tags, and a single molecule may accordingly include multiple tags. In some embodiments, a unique tag can be a synthetic or a unique sequence of natural nucleotides that allows for easy identification of the target polynucleotide within a complicated pool of oligonucleotides containing various sequences. In certain embodiments, unique identifiers are attached to the nucleic acid fragments prior to attaching the adapter sequences. In a some embodiments, unique marker identifiers are contained within adapter sequences such that the unique marker sequence is partially contained in the sequencing reads obtained from boundaries of long fragments. This ensures that homologous fragments can be detected based upon the unique markers that are attached to each fragment, thus further providing for unambiguous reconstruction of a consensus sequence. Homologous fragments may occur for example by chance due to genomic repeats, two fragments originating homologous chromosomes, or fragments originating from overlapping locations on the same chromosome. Such fragments may be discarded to ensure that long fragment assembly can be computed unambiguously. The markers may be attached as described above for the adapter sequences. The markers may be included in the adapter sequences.

In some cases, samples may need multiple additional manipulations. An adapter, such as one described above, with a multiple cloning site identification element may be used for additional steps. A multiple cloning site, is a short segment of DNA which contains many, for example up to ~20 restriction enzyme recognition sites. This feature in the adapter can be used for iterative rounds of molecular cloning or subcloning to allow for insertion of a piece of DNA or several pieces of DNA into the multiple cloning site identification elements. This method can be used to vary the ratio of the target polynucleotide and adapter sequences. Alternatively, it can be used to tailor an adapter sequence with specific identification elements within the adapter. In another embodiment, one can modify or concatenate particular identification elements comprising the adapter using nicked or single nucleotide regions site contained in the adapter identification element.

In some applications, parallel amplification of the target polynucleotides is desirable. End adapters with a universal priming site for a DNA polymerase may be utilized for parallel amplification. With adapters located at each end, the target polynucleotides can be simultaneously amplified using universal primers that are sufficiently complementary to a universal priming site allowing for hybridization to upstream and downstream universal priming sequences in the adapters.

In some instances, more controlled amplification of a target polynucleotide may be facilitated, by using an adapter comprising a specific recognition site for a transcription factor. Specifically, an adapter containing a specific transcriptional promoter sequence that is recognized by a particular polymerase can be utilized. Examples of such polymerases include, but are not limited to T7, T3, SP6, or homologues thereof. Such methods can further be employed when it is desirable to transform a single stranded molecule into a double stranded molecule.

In some embodiments, the adapter sequences can contain a molecular binding site identification element to facilitate identification and isolation of the target polynucleotide for downstream applications. Molecular binding as affinity mechanism allows for the interaction between two molecules to result in a stable association complex. Molecules that can participate in molecular binding reactions include: proteins, nucleic acids, carbohydrates, lipids, and small organic molecules such as ligands, peptides or drugs.

One example of protein-protein molecular binding is affinity mechanism is the avidin-biotin system. Avidin, has a high binding affinity for the molecule, biotin. A biotinylated adapter may be used in the intermediate polynucleotide by synthesizing the adapter sequence with biotinyalted-dNTPs, which are well known in the art. Following the ligation of the target polynucleotide to the biotinaltyed adapters, the biotinaltyed target polynucleotide can be captured using streptavidin magnetic beads. In another embodiment, the molecular binding site is selected from the group consisting of, digoxigenin, a hapten, a ligand, a peptide and a nucleic acid.

When a nucleic acid molecular binding site is used as part of the adapter, it can be used to employ selective hybridization to isolate the target sequence. Selective hybridization may restrict substantial hybridization to target polynucleotides containing the adapter with the molecular binding site and capture nucleic acids, which are sufficiently complementary to the molecular binding site. Thus, through "selective hybridization" one can detect the presence of the target polynucleotide in an unpure sample containing a pool of many polynucleotides. An example of a nucleotide-nucleotide selective hybridization isolation system comprises a system with several capture nucleotides, which are complementary sequences to the molecular binding identification elements, and are optionally immobilized to a solid support. In other embodiments, the capture polynucleotides could be complementary to the target sequences itself or a barcode or unique tag contained within the adapter. The capture polynucleotides can be immobilized to various solid supports, such as inside of a well of a plate, mono-dispersed spheres, microarrays, or any other suitable support surface known in the art. The hybridized complementary adapter polynucleotides attached on the solid support can be isolated, by washing away the undesirable non-binding polynucleotides, leaving the desirable target polynucleotides behind. If complementary adapter molecules are fixed to paramagnetic spheres or similar bead technology for isolation, then spheres can then be mixed in a tube together with the target polynucleotide containing the adapters. When the adapter sequences have been hybridized with the complementary sequences fixed to the spheres, undesirable molecules can be washed away while spheres are kept in the tube with a magnet or similar agent. The desired target molecules can be subsequently released by increasing the temperature, changing the pH, or by using any other suitable elution method known in the art.

In some embodiments, the adapter comprises a nicked adapter. Accordingly, the adapter may contain a single-stranded region within a predominantly double stranded adapter. Such single-stranded regions can take the form of gaps interior to a duplex, or alternatively can be located at the ends forming terminal single-stranded regions. Nicked adapters can be made by several methods. One method is by the use of nickases. Nickases are endonucleases that recognize a specific recognition sequence in double-stranded nucleic acid molecules, and cut one strand at a specific location relative to the recognition sequence, thereby giving rise to single-stranded gaps in duplex DNA. The nicking enzyme may nick one or more of a DNA duplex, an RNA/DNA hybrid and an RNA duplex. Three major sources obtaining sequence-specific DNA nicking enzymes include nicking enzymes from Chlorella algae viruses, from which N.CviQXI (CviNY2A) and N.CviPII (CviNYSI) were originally found (Zhang Y. et al. Virology, 240:366-375 (1998); Xia Y. et al. Nucl. Acids Res. 16:9477-9487 (1988)), bacteria in which N.BstNBI and N.BstSEI were discovered (Morgan R. D. et al. Biol. Chem. 381:1123-5 (2000); Abdurashitov, et al., Mol. Biol. (Mosk) 30:1261-1267 (1996)), and enzymes generated by protein engineering from existing Type IIA restriction enzymes. Examples of nickases that can be used include but are not limited to Nb.BsrDI, Nb.BsmI, Nt.BbvCI, Nb.Bbv.Nb.BtsI and Nt.BstNBI. Site-specific DNA nicking endonucleases are used to form the single-stranded regions by nicking at the boundaries of the single-strand regions, either on opposing DNA strands (creating terminal single-stranded regions) or on the same strand (creating a single-strand gap). The skilled artisan will appreciate that any other site-specific nicking enzyme would give equivalent results. In other aspect of the invention, a nicked adapter can be made by incorporating uracil into one strand of an adaptor sequence and nicking is accomplished subsequently by using uracil-DNA glycosylase which acts by liminating uracil from DNA molecules by cleaving the N-glycosylic bond.

In other aspects of the invention, nicked regions can also be used for several applications including: joining, detecting, cutting and purifying the unpaired adapter regions containing the nick site. Such application can be carried out by restriction enzymes which preferentially cleave single stranded nucleic acids. In one aspect the nicked adapter can used to make a preferred cleavage site for a restriction endonuclease thereby linearizing the circularized polynucleotide. In general, various restriction enzymes can cut single stranded nucleic acids under the correct conditions. Examples of restriction endonucleases that preferentially cleave single-stranded nucleotide regions include, but are not limited, HhaI and CfoI, or equivalents thereof. Alternatively, a general restriction enzyme can be employed to cleave single stranded nucleic acids.

Single-stranded nicked regions within the adapter can facilitate the assembly of multiple nucleic acid fragments and intermediate polynucleotides. This is useful in the construction of intermediate polynucleotide with particular adapter identification elements discussed herein. These applications include strand displacement DNA amplification. Strand displacement DNA amplification, includes introducing a specific nick in the target polynucleotide by a nicking enzyme. Strand displacement DNA polymerase or other equivalent DNA polymerases can initiate a new strand synthesis at the nick and displace the nicked strand, resulting in linear DNA amplification products.

Nicked DNA can also be used to facilitate recombinant DNA technology for gene fragment assembly. Staggered nicks can be introduced in top and bottom strands to generate large cohesive ends (e.g. 8 to 20 nt long). The complementary cohesive ends can anneal together and bypass the ligation step. Nicking enzymes can also be used in preparation of ssDNA ends for DNA fragment assembly in linear or circular form. Strand-specific DNA nicking enzymes can be used to form single-stranded regions by nicking at the boundaries of the single-stranded regions, either on opposing DNA strands, creating terminal single-stranded regions, or on the same strand, creating single-stranded gap regions. Duplex DNA containing a single nick exhibits altered migration through agarose or ploycrylamide gel-based assays. The altered migration characteristic can be used for isolation and purification of the target polynucleotide using standard nucleic acid purification techniques known in the art.

The ligation may be blunt ended or via use of complementary over hanging ends. In certain embodiments, following fragmentation, the ends of the fragments may be repaired, trimmed (e.g. using an exonuclease), or filled (e.g., using a polymerase and dNTPs), to form blunt ends. Upon generating blunt ends, the ends may be treated with a polymerase and dATP to form a template independent addition to the 3'-end and the 5-end of the fragments, thus producing a single A overhanging. This single A is used to guide ligation of fragments with a single T overhanging from the 5'-end in a method referred to as T-A cloning.

Alternatively, because the possible combination of overhangs left by the restriction enzymes are known after a restriction digestion, the ends may be left as is, i.e., ragged ends. In certain embodiments double stranded oligonucleotides with complementary overhanging ends are used.

In certain embodiments, unique marker identifiers are attached to the nucleic acid fragments prior to attaching the adapter sequences. In a preferred embodiment, unique marker identifiers, such as barcodes, are contained within adapter sequences such that the unique marker sequence is partially contained in the sequencing reads obtained from boundaries of long fragments. This ensures that homologous fragments can be detected based upon the unique markers that are attached to each fragment, thus further providing for unambiguous reconstruction of a consensus sequence. Homologous fragments may occur by chance due to genomic repeats, two fragments originating homologous chromosomes, or fragments originating from overlapping locations on the same chromosome. Such fragments may be discarded to ensure that long fragment assembly can be computed unambiguously. The markers may be attached as described above for the adapter sequences. The markers may be included in the adapter sequences.

In other embodiments, end markers can be attached by circularizing long fragments and using a pool of circularization adapters that contain matched pairs of known sequences that are ligated to opposite ends of long fragments, such paired adapters are attached to long fragments which allows to validate long fragment assembly by checking whether a correctly matching pair of adapters is found on opposite ends of the reconstructed fragment (FIGS. 5A-B).

FIGS. 5A-B show an embodiment in which a short bar code (for example 4 bp) is added to the end markers. In certain embodiments, the same end-signal bar code is on both sides of the 10 kb molecule. Thus, after assembling the 10 kb reads, one can tell that there's no misassembly by making sure that the two ends have the same bar code. In other embodiments, the bar codes on both ends are different. In these embodiments, it is only important that the relationship between the two bar codes be known. So one could use a set of bar codes, for example "A-primer-B" and "Q-primer-R" (here A, B, Q, and R represent a short bar code, e.g. 4-nt long sequence), as long as the links A-B and Q-R are known.

In certain embodiments, ligation is used to place the same barcode on both sides (FIG. 5A, bar codes are denoted "A" and the results goes "A-primer-A"). The nucleic acid is then circularize and amplified from the primer site in the middle (in both directions; FIG. 5A). Alternatively, one could ligate a construct of the form "A-primer1-restriction-primer2-A" and then after circularization use a restriction enzyme to cut at the "restriction" size, followed by PCR of primer1 and primer2 to amplify (FIG. 5B).

As used herein, the term "barcode" refers to a known nucleic acid sequence that allows some feature of a polynucleotide with which the barcode is associated to be identified. In some embodiments, the feature of the polynucleotide to be identified is the sample from which the polynucleotide is derived. In some embodiments, barcodes are at least 3, 4, 5, 6, 7, 8, 9, 10, 11, 12, 13, 14, 15, or more nucleotides in length. In some embodiments, barcodes are shorter than 10, 9, 8, 7, 6, 5, or 4 nucleotides in length. In some embodiments, barcodes associated with some polynucleotides are of different length than barcodes associated with other polynucleotides. In general, barcodes are of sufficient length and comprise sequences that are sufficiently different to allow the identification of samples based on barcodes with which they are associated. In some embodiments, a barcode, and the sample source with which it is associated, can be identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some embodiments, each barcode in a plurality of barcodes differ from every other barcode in the plurality at least two nucleotide positions, such as at least 2, 3, 4, 5, 6, 7, 8, 9, 10, or more positions. In some embodiments, both a first adapter and a second adapter comprise at least one of a plurality of barcode sequences. In some embodiments, barcodes for second adapter oligonucleotides are selected independently from barcodes for first adapter oligonucleotides. In some embodiments, first adapter oligonucleotides and second adapter oligonucleotides having barcodes are paired, such that adapters of the pair comprise the same or different one or more barcodes. In some embodiments, the methods of the invention further comprise identifying the sample from which a target polynucleotide is derived based on a barcode sequence to which the target polynucleotide is joined. In general, a barcode may comprise a nucleic acid sequence that when joined to a target polynucleotide serves as an identifier of the sample from which the target polynucleotide was derived.

Methods of the invention involve determining an amount of amplifiable nucleic acid present in a sample. This step allows one to establish the amount amplifiable fragments in order to choose a proper dilution amount to for partitioning. The proper dilution amount reduces the amount of molecules per partition to reduce the complexity of nucleic acid sequences to aid sequence assembly downstream. Any known method may be used to quantify amplifiable nucleic acid, and an exemplary method is the polymerase chain reaction (PCR), specifically quantitative polymerase chain reaction (QPCR). QPCR is a technique based on the polymerase chain reaction, and is used to amplify and simultaneously quantify a targeted nucleic acid molecule. QPCR allows for both detection and quantification (as absolute number of copies or relative amount when normalized to DNA input or additional normalizing genes) of a specific sequence in a DNA sample. The procedure follows the general principle of polymerase chain reaction, with the additional feature that the amplified DNA is quantified as it accumulates in the reaction in real time after each amplification cycle. QPCR is described, for example, in Kurnit et al. (U.S. Pat. No. 6,033,854), Wang et al. (U.S. Pat. Nos. 5,567,583 and 5,348,853), Ma et al. (The Journal of American Science, 2(3), 2006), Heid et al. (Genome Research 986-994, 1996), Sambrook and Russell (Quantitative PCR, Cold Spring Harbor Protocols, 2006), and Higuchi (U.S. Pat. Nos. 6,171,785 and 5,994,056). The contents of these are incorporated by reference herein in their entirety.

Two common methods of quantification are: (1) use of fluorescent dyes that intercalate with double-stranded DNA, and (2) modified DNA oligonucleotide probes that fluoresce when hybridized with a complementary DNA. In the first method, a DNA-binding dye binds to all double-stranded (ds)DNA in PCR, resulting in fluorescence of the dye. An increase in DNA product during PCR therefore leads to an increase in fluorescence intensity and is measured at each cycle, thus allowing DNA concentrations to be quantified. The reaction is prepared similarly to a standard PCR reaction, with the addition of fluorescent (ds)DNA dye. The reaction is run in a thermocycler, and after each cycle, the levels of fluorescence are measured with a detector; the dye only fluoresces when bound to the (ds)DNA (i.e., the PCR product). With reference to a standard dilution, the (ds)DNA concentration in the PCR can be determined. Like other real-time PCR methods, the values obtained do not have absolute units associated with it. A comparison of a measured DNA/RNA sample to a standard dilution gives a fraction or ratio of the sample relative to the standard, allowing relative comparisons between different tissues or experimental conditions. To ensure accuracy in the quantification, it is important to normalize expression of a target gene to a stably expressed gene. This allows for correction of possible differences in nucleic acid quantity or quality across samples.

The second method uses a sequence-specific RNA or DNA-based probe to quantify only the DNA containing the probe sequence; therefore, use of the reporter probe significantly increases specificity, and allows quantification even in the presence of some non-specific DNA amplification. This allows for multiplexing, i.e., assaying for several genes in the same reaction by using specific probes with differently colored labels, provided that all genes are amplified with similar efficiency.

This method is commonly carried out with a DNA-based probe with a fluorescent reporter (e.g. 6-carboxyfluorescein) at one end and a quencher (e.g., 6-carboxy-tetramethylrhodamine) of fluorescence at the opposite end of the probe. The close proximity of the reporter to the quencher prevents detection of its fluorescence. Breakdown of the probe by the 5' to 3' exonuclease activity of a polymerase (e.g., Taq polymerase) breaks the reporter-quencher proximity and thus allows unquenched emission of fluorescence, which can be detected. An increase in the product targeted by the reporter probe at each PCR cycle results in a proportional increase in fluorescence due to breakdown of the probe and release of the reporter. The reaction is prepared similarly to a standard PCR reaction, and the reporter probe is added. As the reaction commences, during the annealing stage of the PCR both probe and primers anneal to the DNA target. Polymerization of a new DNA strand is initiated from the primers, and once the polymerase reaches the probe, its 5'-3'-exonuclease degrades the probe, physically separating the fluorescent reporter from the quencher, resulting in an increase in fluorescence. Fluorescence is detected and measured in a real-time PCR thermocycler, and geometric increase of fluorescence corresponding to exponential increase of the product is used to determine the threshold cycle in each reaction.

Relative concentrations of DNA present during the exponential phase of the reaction are determined by plotting fluorescence against cycle number on a logarithmic scale (so an exponentially increasing quantity will give a straight line). A threshold for detection of fluorescence above background is determined. The cycle at which the fluorescence from a sample crosses the threshold is called the cycle threshold, $C_t$. Since the quantity of DNA doubles every cycle during the exponential phase, relative amounts of DNA can be calculated, e.g. a sample with a $C_t$ of 3 cycles earlier than another has $2^3=8$ times more template. Amounts of nucleic acid (e.g., RNA or DNA) are then determined by comparing the results to a standard curve produced by a real-time PCR of serial dilutions (e.g. undiluted, 1:4, 1:16, 1:64) of a known amount of nucleic acid.

In certain embodiments, the QPCR reaction involves a dual fluorophore approach that takes advantage of fluorescence resonance energy transfer (FRET), e.g., LIGHTCYCLER hybridization probes, where two oligonucleotide probes anneal to the amplicon (e.g. see U.S. Pat. No. 6,174,670). The oligonucleotides are designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: SCORPIONS probes (e.g., Whitcombe et al., Nature Biotechnology 17:804-807, 1999, and U.S. Pat. No. 6,326,145), Sunrise (or AMPLIFLOUR) primers (e.g., Nazarenko et al., Nuc. Acids Res. 25:2516-2521, 1997, and U.S. Pat. No. 6,117,635), and LUX primers and MOLECULAR BEACONS probes (e.g., Tyagi et al., Nature Biotechnology 14:303-308, 1996 and U.S. Pat. No. 5,989,823).

In other embodiments, the QPCR reaction uses fluorescent Taqman methodology and an instrument capable of measuring fluorescence in real time (e.g., ABI Prism 7700 Sequence Detector). The Taqman reaction uses a hybridization probe labeled with two different fluorescent dyes. One dye is a reporter dye (6-carboxyfluorescein), the other is a quenching dye (6-carboxy-tetramethylrhodamine). When the probe is intact, fluorescent energy transfer occurs and the reporter dye fluorescent emission is absorbed by the quenching dye. During the extension phase of the PCR cycle, the fluorescent hybridization probe is cleaved by the 5'-3' nucleolytic activity of the DNA polymerase. On cleavage of the probe, the reporter dye emission is no longer transferred efficiently to the quenching dye, resulting in an increase of the reporter dye fluorescent emission spectra. Any nucleic acid quantification method, including real-time methods or single-point detection methods may be use to quantify the amount of nucleic acid in the sample. The detection can be performed several different methodologies (e.g., staining, hybridization with a labeled probe; incorporation of biotinylated primers followed by avidin-enzyme conjugate detection; incorporation of 32P-labeled deoxynucleotide triphosphates, such as dCTP or dATP, into the amplified segment), as well as any other suitable detection method known in the art for nucleic acid quantification. The quantification may or may not include an amplification step.

The results of the quantitation can be used to determine the proper dilution for partitioning before the sequencing steps. The quantitation may not be experimental. The amount of nucleic acid in the pre-partitioned sample can be determined using various methods or the sample may be supplied with the amount of nucleic acid predetermined. In various embodiments, the fractioned sample is amplified, e.g. using a PCR step. Particularly, the fragmented nucleic acids are partitioned based upon results of the determining step such that each partitioned portion includes, on average, a subset of unique sequences. Limiting the number of amplifiable molecules per partitioned portion greatly reduces or eliminates chances of having a repeated sequence within a partitioned portion. Thus, sample complexity within each partitioned portion is significantly reduced as compared to the original sample, which allows for unambiguous reconstruction of a consensus sequence.

In certain embodiments, the partitioning is performed under microfluidic control. In other embodiments, partitioning involves dispensing the sample into different wells of a microwell plate. Such diluting and dispensing is described for example in Brown et al. (U.S. Pat. Nos. 6,143,496 and 6,391,559), the content of each of which is incorporated by reference herein in its entirety. In certain embodiments, there is, on average, only a single nucleic acid fragment in each well.

In other embodiments, partitioning involves segmenting the sample into droplets. In certain embodiments, there is only a single nucleic acid fragment in each droplet. Droplet forming methods are known in the art and described for example in Davies et al. (U.S. Pat. Nos. 7,993,911; 7,622,076 and U.S. patent application numbers 2010/0304446; 2010/0109320; 2010/0092973; 2010/0075312; and 2008/0277494); Griffiths et al. (U.S. Pat. Nos. 6,489,103; 6,808,882; 7,138,233; 7,252,943; 7,582,446; 7,638,276; 7,897,341; and 7,968,287 and U.S. patent application numbers 2010/0210479; 2009/0325236; and 2009/0197772); Link et al. (U.S. patent application numbers 2011/0000560; 2010/0137163; and 2010/0105866); Stone et al. (U.S. Pat. No. 7,708,949 and U.S. patent application number 2010/0172803), and Anderson et al. (U.S. Pat. No. 7,041,481 and which reissued as RE41,780), the content of each of which is incorporated by reference herein in its entirety.

Generally, a sample fluid becomes dispersed into co-flowing streams of an immiscible fluid, such as an oil) to form monodisperse droplets. These droplets can be flowed through channels and reactions can be conducted in the droplets. Briefly, droplet forming devices generally include an inlet channel, and outlet channel, and at least one carrier fluid channel. The channels are configured to meet at a junction. The inlet channel flows sample fluid to the junction, and the carrier fluid channels flow a carrier fluid that is immiscible with the sample fluid to the junction. The inlet channel narrows at its distal portion where it connects to the junction. The inlet channel is oriented to be perpendicular to the carrier fluid channels. Droplets are formed as sample fluid flows from inlet channel to the junction, where the sample fluid interacts with the flowing carrier fluid provided to the junction by carrier fluid channels, thus forming droplets of sample fluid in the carrier fluid that flow to the outlet channel.

The fragmented nucleic acids are then amplified in each partitioned portion. Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, polymerase chain reaction-single strand conformation polymorphism, ligase chain reaction (Barany F. (1991) PNAS 88:189-193; Barany F. (1991) PCR Methods and Applications 1:5-16), ligase detection reaction (Barany F. (1991) PNAS 88:189-193), strand displacement amplification and restriction fragments length polymorphism, transcription based amplification system, nucleic acid sequence-based amplification, rolling circle amplification, and hyper-branched rolling circle amplification.

In certain embodiments, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. The primers are complementary to their respective strands of the double stranded target sequence.

In particular embodiments, PCR is used to amplify DNA molecules after they are dispensed into individual partitions. In some cases, one or more specific priming sequences within amplification adapters are utilized for PCR amplification. The amplification adapters may be ligated to fragmented DNA molecules before or after dispensing into individual partitions. Nucleic acids that include amplification adapters with suitable priming sequences on both ends can be PCR amplified exponentially. Typically, nucleic acids with only one suitable priming sequence, for example due to imperfect ligation efficiency of amplification adapters comprising priming sequences would only undergo linear amplification. Further, nucleic acids can be eliminated from amplification, for example PCR amplification, all together, if adapters with priming sequences are not ligated. In some embodiments, the number of PCR cycles vary between 10-30, but can be as low as 9, 8, 7, 6, 5, 4, 3, 2 or less or as high as 40, 45, 50, 55, 60 or more. As a result, exponentially amplifiable fragments carrying amplification adapters with a suitable priming sequence can be present in much higher (1000 fold or more) concentration compared to linearly amplifiable or un-amplifiable fragments, after a PCR amplification.

PCR, as compared to whole genome amplification techniques (such as amplification with randomized primers or Multiple Displacement Amplification (MDA)), includes, for example, the following benefits. More uniform relative sequence coverage is obtained with PCR because each fragment can be copied at most once per cycle and amplification is controlled by thermocycling program. In addition, PCR has a substantially lower rate of forming chimeric molecules than, for example, MDA. This is desirable because chimeric molecules pose significant challenge for accurate sequence assembly by presenting non-biological sequences in the assembly graph, which can result in higher rate of misassemblies or highly ambiguous and fragmented assembly. (Lasken et al, 2007, BMC Biotechnology). Further, amplification adaptors of the invention with specific priming sites of a fixed sequence reduce sequence specific biases that may result from binding of randomized primers commonly used in MDA. Also, PCR provides higher reproducibility in amount of final amplified DNA product which can be controlled by selection of the number of PCR cycles. Further, polymerases commonly used in PCR are also known to have higher fidelity in replication as compared to common whole genome amplification techniques.

Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and, length of the primer pairs yield the desired melting temperature. The simplest equation for determining the melting temperature of primers smaller than 25 base pairs is the Wallace Rule (Td=2(A+T)+4(G+C)). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Oligo Design, available from Invitrogen Corp.

To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one cycle; there can be numerous cycles) to obtain a high concentration of an amplified segment of a desired target sequence. The length of the amplified segment of the desired target sequence is determined by relative positions of the primers with respect to each other, and therefore, this length is a controllable parameter.

With PCR, it is possible to amplify a single copy of a specific target sequence in genomic DNA to a level that can be detected by several different methodologies (e.g., staining, hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences can be used to obtain segments of DNA (e.g., genes) for insertion into recombinant vectors.

Methods for performing PCR in droplets are shown for example in Link et al. (U.S. patent application numbers 2008/0014589, 2008/0003142, and 2010/0137163) and Anderson et al. (U.S. Pat. No. 7,041,481 and which reissued as RE41,780), the content of each of which is incorporated by reference herein in its entirety.

Other amplification methods and strategies can also be utilized to detect nucleic acids in biological fluids. For example, another approach would be to combine PCR and the ligase chain reaction (LCR). Since PCR amplifies faster than LCR and requires fewer copies of target DNA to initiate, PCR can be used as first step followed by LCR. The amplified product could then be used in a LCR or ligase detection reaction (LDR) in an allele-specific manner that would indicate if a mutation was present. Another approach is to use LCR or LDR for both amplification and allele-specific discrimination. The later reaction is advantageous in that it results in linear amplification. Thus the amount of amplified product is a reflection of the amount of target DNA in the original specimen and therefore permits quantitation.

LCR utilizes pairs of adjacent oligonucleotides which are complementary to the entire length of the target sequence (Barany F. (1991) PNAS 88:189-193; Barany F. (1991) PCR Methods and Applications 1:5-16). If the target sequence is perfectly complementary to the primers at the junction of these sequences, a DNA ligase will link the adjacent 3' and 5' terminal nucleotides forming a combined sequence. If a thermostable DNA ligase is used with thermal cycling, the combined sequence will be sequentially amplified. A single base mismatch at the junction of the oligonucleotides will preclude ligation and amplification. Thus, the process is allele-specific. Another set of oligonucleotides with 3' nucleotides specific for the mutant would be used in another reaction to identify the mutant allele. A series of standard conditions could be used to detect all possible mutations at any known site. LCR typically utilizes both strands of genomic DNA as targets for oligonucleotide hybridization with four primers, and the product is increased exponentially by repeated thermal cycling.

A variation of the reaction is the ligase detection reaction (LDR) which utilizes two adjacent oligonucleotides which are complementary to the target DNA and are similarly joined by DNA ligase (Barany F. (1991) PNAS 88:189-193). After multiple thermal cycles the product is amplified in a linear fashion. Thus the amount of the product of LDR reflects the amount of target DNA. Appropriate labeling of the primers allows detection of the amplified product in an allele-specific manner, as well as quantitation of the amount of original target DNA. One advantage of this type of reaction is that it allows quantitation through automation (Nickerson et al. (1990) PNAS 87: 8923-8927).

The amplified nucleic acid in each partitioned portion may then be fragmented. Bar code sequences may be attached to these fragments. In various embodiments, the bar code sequences label the nucleic acid fragments in a partition specific manner. Lengths and sequences of bar code sequences can be designed to achieve a desired level of accuracy determining the identity of the partition. Bar code sequences can be designed such that after a tolerable number of point mutations, the identity of the partition can still be deduced with a desired accuracy. The amplified nucleic acid may be fragmented or sheared to a desired length using a variety of mechanical, chemical and/or enzymatic methods. In certain embodiments, a Tn-5 transposase (commercially available from Epicentre Biotechnologies; Madison, Wis.) cuts the amplified nucleic acid into fragments and inserts short pieces of DNA into the cuts. The short pieces of DNA are used to incorporate the bar code sequences.

Attaching bar code sequences to nucleic acid templates is shown in Kahvejian et al. (U.S. patent application number 2008/0081330), and Steinman et al. (International patent application number PCT/US09/64001), the content of each of which is incorporated by reference herein in its entirety. Methods for designing sets of bar code sequences and other methods for attaching bar code sequences are shown in U.S. Pat. Nos. 6,138,077; 6,352,828; 5,636,400; 6,172,214; 6235, 475; 7,393,665; 7,544,473; 5,846,719; 5,695,934; 5,604,097; 6,150,516; RE39,793; 7,537,897; 6172,218; and 5,863,722, the content of each of which is incorporated by reference herein in its entirety. In certain embodiments, a single bar code is attached to each fragment. In other embodiments, a plurality of bar codes, e.g., two bar codes, are attached to each fragment.

The bar code sequence generally includes certain features that make the sequence useful in sequencing reactions. For example the bar code sequences are designed to have minimal or no homopolymer regions, i.e., 2 or more of the same base in a row such as AA or CCC, within the bar code sequence. The bar code sequences are also designed so that they are at least one edit distance away from the base addition order when performing base-by-base sequencing, ensuring that the first and last base do not match the expected bases of the sequence.

The bar code sequences are designed such that each sequence is correlated to nucleic acid in a particular portioned portion, allowing sequence reads to be correlated back to the partitioned portion from which they came. Methods of designing sets of bar code sequences is shown for example in Brenner et al. (U.S. Pat. No. 6,235,475), the contents of which are incorporated by reference herein in their entirety. In certain embodiments, the bar code sequences range from about 5 nucleotides to about 15 nucleotides. In a particular embodiment, the bar code sequences range from about 4 nucleotides to about 7 nucleotides. Since the bar code sequence is sequenced along with the template nucleic acid, the oligonucleotide length should be of minimal length so as to permit the longest read from the template nucleic acid attached. Generally, the bar code sequences are spaced from the template nucleic acid molecule by at least one base (minimizes homopolymeric combinations).

Methods of the invention involve attaching the bar code sequences to the template nucleic acids. In certain embodiments, the bar code sequences are attached to the template nucleic acid molecule with an enzyme. The enzyme may be a ligase or a polymerase. The ligase may be any enzyme capable of ligating an oligonucleotide (RNA or DNA) to the template nucleic acid molecule. Suitable ligases include T4 DNA ligase and T4 RNA ligase (such ligases are available commercially, from New England Biolabs). Methods for using ligases are well known in the art. The polymerase may be any enzyme capable of adding nucleotides to the 3' and the 5' terminus of template nucleic acid molecules.

The ligation may be blunt ended or via use of complementary over hanging ends. In certain embodiments, following fragmentation, the ends of the fragments may be repaired, trimmed (e.g. using an exonuclease), or filled (e.g., using a polymerase and dNTPs), to form blunt ends. Upon generating blunt ends, the ends may be treated with a polymerase and dATP to form a template independent addition to the 3'-end and the 5-end of the fragments, thus producing a single A overhanging. This single A is used to guide ligation of fragments with a single T overhanging from the 5'-end in a method referred to as T-A cloning.

Alternatively, because the possible combination of overhangs left by the restriction enzymes are known after a restriction digestion, the ends may be left as is, i.e., ragged ends. In certain embodiments double stranded oligonucleotides with complementary over hanging ends are used. In particular embodiments, bar code sequences are incorporated using limited cycle PCR.

According to some embodiments of the invention, the templates are sequenced after incorporating bar codes to nucleic acid templates. Various methods can be used to determine the identity of a partition allowing for easier assembly of sequences into larger fragments. In some embodiments, the partitions remain physically separated. In some embodiments, the nucleic acids are labeled with a dye. Appropriate numbers of partitions can be pooled together allowing for the identification of the partition origin of a sequence. The number of partitions that can be pooled together while allowing for the identification of the partition origin of a nucleic acid sequence may depend on the method of labeling the nucleic acids. Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes.

A sequencing technique that can be used in the methods of the provided invention includes, for example, Helicos True Single Molecule Sequencing (tSMS) (Harris T. D. et al.

(2008) Science 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step. Further description of tSMS is shown for example in Lapidus et al. (U.S. Pat. No. 7,169,560), Lapidus et al. (U.S. patent application number 2009/0191565), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety.

Another example of a DNA sequencing technique that can be used in the methods of the provided invention is 454 sequencing (Roche) (Margulies, M et al. 2005, Nature, 437, 376-380). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used in the methods of the provided invention is SOLiD technology (Applied Biosystems). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a DNA sequencing technique that can be used in the methods of the provided invention is Ion Torrent sequencing (U.S. patent application numbers 2009/0026082, 2009/0127589, 2010/0035252, 2010/0137143, 2010/0188073, 2010/0197507, 2010/0282617, 2010/0300559), 2010/0300895, 2010/0301398, and 2010/0304982), the content of each of which is incorporated by reference herein in its entirety. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and is attached at a resolution such that the fragments are individually resolvable. Addition of one or more nucleotides releases a proton ($H^+$), which signal detected and recorded in a sequencing instrument. The signal strength is proportional to the number of nucleotides incorporated.

Another example of a sequencing technology that can be used in the methods of the provided invention is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a sequencing technology that can be used in the methods of the provided invention includes the single molecule, real-time (SMRT) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off.

Detection of the corresponding fluorescence of the dye indicates which base was incorporated. The process is repeated.

Another example of a sequencing technique that can be used in the methods of the provided invention is nanopore sequencing (Soni G V and Meller A. (2007) Clin Chem 53: 1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using a chemical-sensitive field effect transistor (chemFET) array to sequence DNA (for example, as described in US Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used in the methods of the provided invention involves using a electron microscope (Moudrianakis E. N. and Beer M. Proc Natl Acad Sci USA. 1965 March; 53:564-71). In one example of the technique, individual DNA molecules are labeled using metallic labels that are distinguishable using an electron microscope. These molecules are then stretched on a flat surface and imaged using an electron microscope to measure sequences.

The obtained sequence reads are then split according to their bar code, i.e., demultiplexed, and reads originating from individual wells are saved into separate files. Fragments amplified within each partitioned portion are then reconstructed using a de-novo assembly or by aligning to known reference sequence if such sequence exists. Methods of the invention take advantage of pair-end reads and sequencing quality scores that represent base calling confidence to reconstruct full length fragments.

To begin the reconstruction process, short reads are stitched together bioinformatically by finding overlaps and extending them. To be able to do that unambiguously, one must ensure that long fragments that were amplified within each partitioned portion are distinct enough, and do not have similar stretches of DNA that will make assembly from short fragments ambiguous, which can occur, for example, if two molecules in the same well originated from overlapping positions on homologous chromosomes, overlapping positions of same chromosome, or genomic repeat. Such fragments can be detected during sequence assembly process by observing multiple possible ways to extend the fragment, one of which contains sequence specific to end marker. End markers can be chosen such that end marker sequence is not frequently found in DNA fragments of sample that is analyzed and probabilistic framework utilizing quality scores can be applied to decide whether a certain possible sequence extension way represents end maker and thus end of the fragment.

Overlapping fragments may be computationally discarded since they no longer represent the same initial long molecule. This process allows to treat population of molecules resulting after amplification as a clonally amplified population of disjoint molecules with no significant overlap or homology, which enables sequencing errors to be corrected to achieve very high consensus accuracy and allows unambiguous reconstruction of long fragments. If overlaps are not discarded, then one has to assume that reads may be originating from fragments originating from two homologous chromosomes or overlapping regions of the same chromosome (in case of diploid organism) which makes error correction difficult and ambiguous.

Computational removal of overlapping fragments also allows use of quality scores to resolve nearly-identical repeats. Resulting long fragments may be assembled into full genomes using any of the algorithms known in the art for genome sequence assembly that can utilize long reads.

In addition to de-novo assembly fragments can be used to obtain phasing (assignment to homologous copies of chromosomes) of genomic variants, by observing that under conditions of experiment described in the preferred embodiment long fragments originate from either one of chromosomes, which enables to correlate and co-localize variants detected in overlapping fragments obtained from distinct partitioned portions.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

EXAMPLES

Example 1

Genome Assembly from Short Sequence Reads

An in vitro protocol was developed that allows amplification sequencing and reassembly of intermediate sized genomics fragments. In brief, genomic DNA was sheared to appropriate fragment size, amplification adapters were ligated at the ends of fragments, and the library was quantitated using qPCR to establish the number of amplifiable DNA fragments. The library was amplified library using adapter-specific primers with PCR after diluting the library to a necessary concentration. Amplification was carried out in independent wells of a PCR plate such that each well had an independent amplified population of molecules. The average number of molecules within each well was kept around 500-1000 to reduce complexity of unique DNA sequences, which is important to aid sequence assembly downstream. The resulting pool of amplified molecules were fragmented into a sequencing library using Nextera DNA transposase, and sequencing adapters with barcodes unique to each well were incorporated through limited cycle PCR. The library was then sequenced. After sequencing, reads were separated according to the barcodes and original long fragments were assembled using developed assembly algorithms described herein.

Methods of the invention allowed highly parallel preparation and sequencing of a large number of individual samples prepared from an artificially limited population of DNA molecules. The resulting complexity bottleneck was important for successful reassembly of the long DNA fragments.

Figure 2:
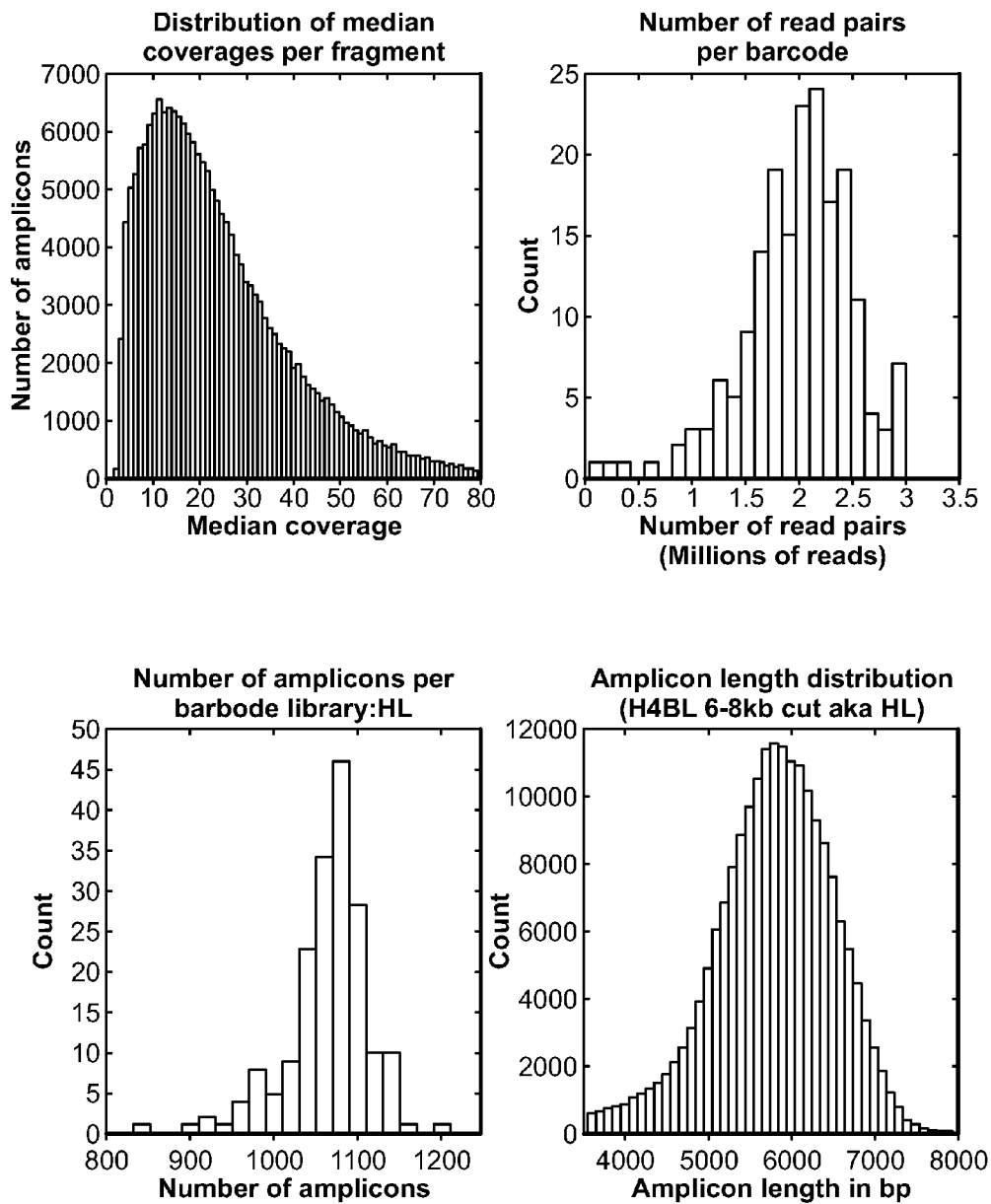
FIG. 2 is a set of graphs showing statistics for a sample, obtained by mapping reads to a reference genome.

To calibrate performance of the method, it was first applied it to sequencing of human genomic DNA. DNA was sheared to 4-8 kb, and a 5-7 kb gel cut was used as starting material for sample preparation. The Library was quantitated using qPCR relative to a set of previously sequenced standards and dilution was chosen to have a mean number of molecules around 1000. In this protocol, 192 barcodes were used, corresponding to wells of two 96 well plates. Barcodes were chosen such that to guarantee that all barcodes were at least two errors away from each other, and all reads that did not match exact barcode sequences were discarded. After sequencing, reads were aligned to a human genome reference, and it was established that an average number of distinct fragments was close to 1000. Fragment length distribution was found to be smaller than the initial gel cut, which can be explained by the fact that last few hundred base pairs from each fragment were underrepresented in the data due to the library construction method. Median coverage per fragment was around 20× which was sufficient to allow de-novo assembly of intermediate sized fragments (FIG. 2).

Figure 3:
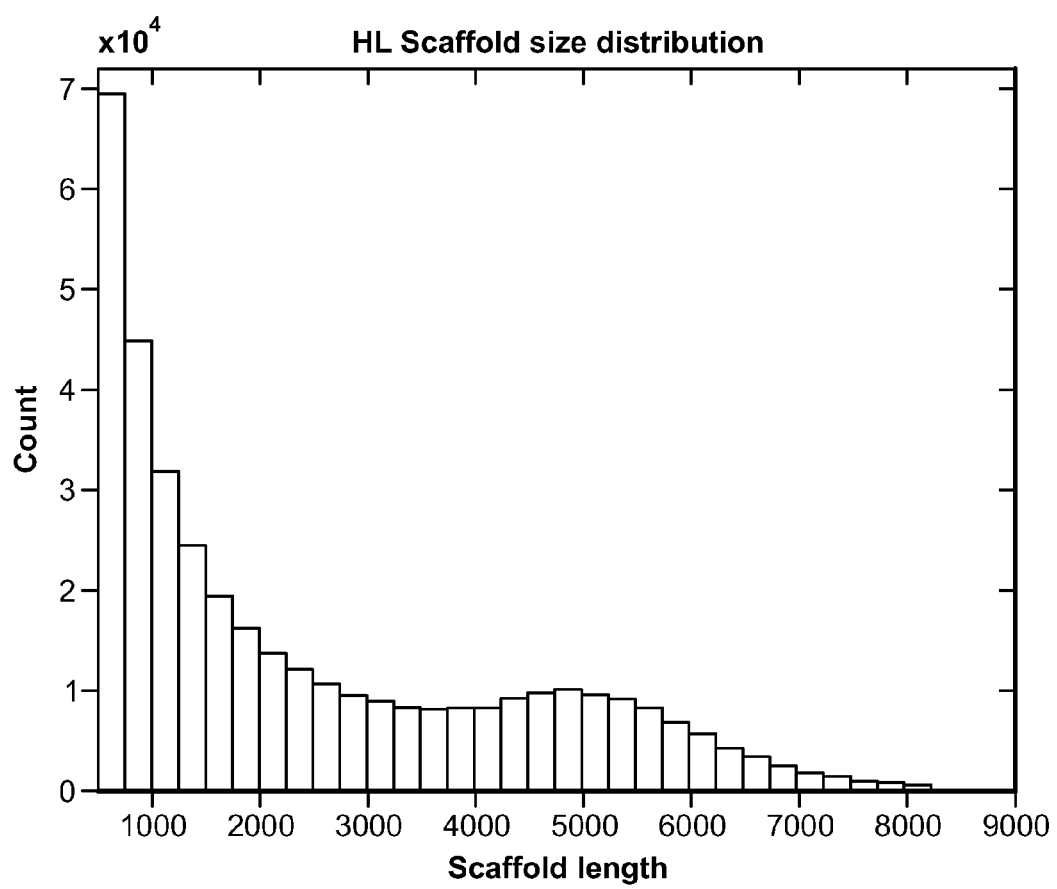
FIG. 3 is a graph showing assembly statistics.

Consensus sequences were assembled as described above. After assembly, a distribution of contigs with median size (N50) of approximately 3.5 kb was obtained. Complete reconstruction of full fragments was not possible for all intermediate sized fragments due to high repeat content of the human genome and variation of coverage due to sampling statistics; however, low frequency repeats were resolved using methods of the invention because it is unlikely that they will appear in multiple wells (FIG. 3).

Due to artificial dilution and amplification of limited amount of molecules, most of the fragments within each partitioned portion were a result of amplification of a fragment originating from a disjoint set of locations on the genome (otherwise overlaps would have been detected by coverage based analysis, or detecting heterozygous variants inconsistent with single molecule amplification, or by analysis of end markers embedded in the amplification adapters). This allowed haplotype-resolved variant calling to be performed by detecting variants using a pipeline that assumes haploid genome and "stitching together" overlapping fragments that share the same variants to obtain longer stretches of phased variants. This can be combined with haplotyping chips and bioinformatics approaches to extend continuous stretches of phased genome.

Figure 4:
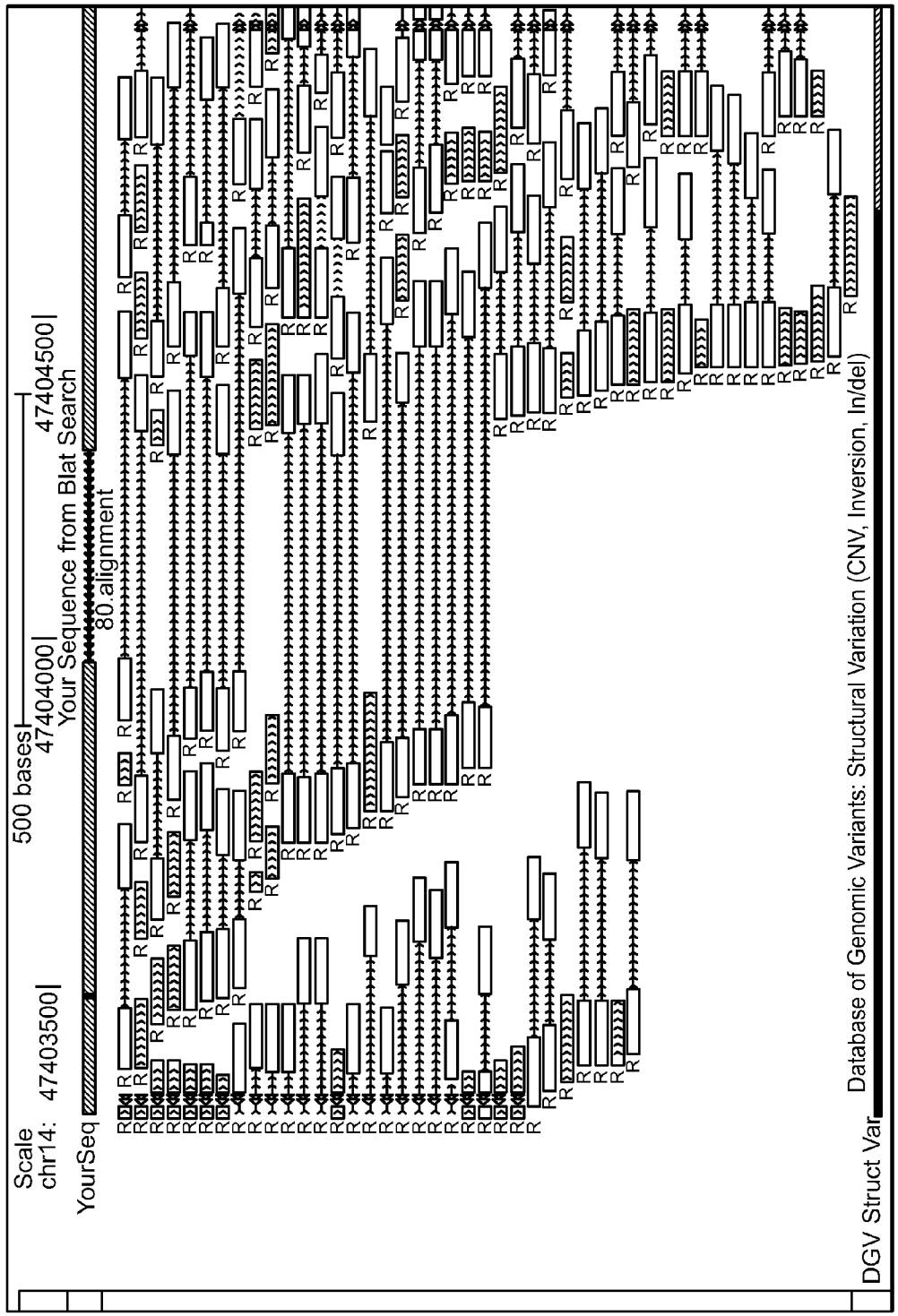
FIG. 4 shows structural variation detected using methods of the invention. Methods of the invention allowed detection of novel variants by comparing assembled long fragments with reference sequences. Single molecule amplification also allowed haplotype-resolved variant calling since each fragment originated from one of two chromosomes.

Methods of the invention were used to detect novel sequences by comparative analysis of assembled intermediate sized fragments (FIG. 4).

Example 2

Sample DNA Preparation

Genomic DNA was prepared using DNAeasy kit and sheared with HydroShear instrument to obtain DNA with size range around 10 kb. Sample was run on 0.8% e-gel to perform initial size selection to select band 7-10 kb band. Sample was analyzed using Agilent Bioanalyzer to confirm size distribution. DNA was treated with NEB end repair kit to obtain blunt end 5' phosphorylated ends.

Example 3

Repair Ends

A New England Biolabs end repair module was used to make blunt ends as follows. In 100 uL volume mix: 10 uL of 10× Neb next End repair reaction buffer, 5 uL of NEB Next End repair enzyme mix, 50 uL of eluted sample, and 35 uL of water. The mixture is incubated for 30 minutes at 20° C. and then purified on a Qiagen column. Elusion was performed in 30 ul water.

Example 4

Ligate Amplification Adaptors

A kit commercially available from 454 Life Sciences was used to ligate adapters onto the fragmented nucleic acid. The two sequence primers below were used:

```
Primer A1:
SEQ ID NO. 1:
5'-CCATCTCATCCCTGCGTGTCTCCGACTCAG-3'

SEQ ID NO. 2:
3'-TCTCCGACTCAG-5'

Primer B:
SEQ ID NO. 3:
5'-/5BioTEG/CCTATCCCCTGTGTGCCTTGGCAGTCTCAG-3'

SEQ ID NO. 4:
3'-TGGCAGTCTCAG-5'
```

Ligation was accomplished as follows. A mix of DNA 10 ul (450 ng); 2× ligation Buffer 20 ul; Adapter mix 5 ul; and Ligase 5 ul was incubated at 25° C. for 15 minutes.

Example 5

DNA Purification

Ampure beads purification was performed after ligation. The ratio of DNA to beads was 1:1.5 (Human DNA 40 ul:60 ul beads). The DNA and beads were gently vortexed by tapping on tube and incubated for 10 minutes. The tubes were then placed on a magnetic rack for 3 minutes and the supernatant was discarded. Two washed were performed with 70% ethanol without removing tubes from the rack. Most of the ethanol was removed and caps were removed from the tubes to allow for air drying until completely dry (approximately 5 minutes). Elution was performed in 25 µl of water. Incubation was for a few minutes and the supernatant was collected.

Example 6

Fill-in Reaction and Size Selection

A mixture of DNA 20 ul; 10× fill in buffer 2.5 ul; dNTP mix 1 ul; fill in polymerase 1.5 ul was prepared and incubated for 20 minutes at 37° C. 20 µL was transferred to the agarose gel and size selection was performed. Samples were cut from Qiagen gel and nucleic acid fragments eluted in 30 ul water.

Example 7

Quantitate Library Using qPCR

To quantitate, the sample library was compared to a reference library of known concentration, using LongAmp polymerase, and the same primer concentration that will be used for the amplification reaction. A mixture of 1.25 uL of 20× EvaGreen dye, 0.5 uL of Rox reference dye in 25 uL reaction volume was prepared. The qPCR was conducted according to the same thermocycling protocol as the used from the PCR reaction, see Table 2.

Example 8

PCR Amplification of Partitioned Nucleic Acids

The PCR reaction mixture is shown in Table 1 below.

TABLE 1

|  | 1rnx | 220rnx |
|---|---|---|
| LONGAMP-V2-LEFT (100 μm) | 0.1 μl | 20 μl |
| LONGAMP-V2-RIGHT (100 μm) | 0.1 μl | 20 μl |
| DNA | x (500 molecules) | x (110k molecules) |
| NEB LongAmp (M0287L) | 12.5 μl | 2750 μl |
| Water | 12.05 μl | 2673 μl |

```
SEQ ID NO. 5: LONGAMP-V2-LEFT
5'-CCA TCT CAT CCC TGC GTG TCT CCG-3'

SEQ ID NO. 6: LONGAMP-V2-RIGHT
5'-CCT ATC CCC TGT GTG CCT TGG CAG T-3'
```

The PCR reaction was conducted as follows. Two 96 half skirt plates were placed on ice to allow them to cool. The PCR cycler was set at 94° C. for preheating. To a 15 mL tube, was added water, both primers, and calculated amount of the sample. This mixture was vortexed rigorously, and placed on ice to cool down. 2× Enzyme master mix was added and the mixture was vortexed rigorously. 25 mL was transferred to a sterile container. Using an 8-channel pipette, the mixture was dispensed across all wells of both plates. The plates were covered with transparent PCR film, quickly spun, placed on the thermocycler, and the PCR reaction was conducted as shown in Table 2 below:

TABLE 2

| Step | Temperature | Time |
|---|---|---|
| 1 | 94 | 0:30 |
| 2 | 94 | 0:15 |
| 3 | 65 | 8:00 |
| 4 | Cycle to step 2 24 times | |
| 5 | 65 | 8:00 |
| 6 | 4 | hold |

Example 9

DNA Purification

A Zymo ZR-96 DNA clean and concentration (Zymogen D4024) kit was used for DNA purification. The two Zymo plates were assembled and the membrane plate was put on top of the collection plate. After the PCR reaction was finished 100 uL of the binding buffer was dispensed into each well and the PCR reaction contents were mixed with DNA binding buffer and transfer it to a Zymo plate. The plates were spun at 2200 g (or more) for 5 minutes, discarding the flow-through. 300 uL of the wash buffer was added to each well. The plates were spun again at 2200 g (or more) for 5 minutes, discarding the flow-through. 300 uL of the wash buffer was added to each well. The plates were spun again at 2200 g (or more) for 5 minutes.

The membrane plate was transferred to an elution plate and the collection plate was discarded. 12 uL of water was added to the middle of each membrane. The plates were spun at 2200 g (or more) for 5 minutes, use slower ramp-up speed (4 instead of 9).

Example 10

Fragmentation

The amplified nucleic acid is then fragmented. Each reaction had: 4 uL of DNA from the previous step eluted in water; 1 uL of 5× high molecular weight buffer, and 4 nL of nextera enzyme Illumina compatible 250 uL of high molecular weight buffer (HMW) and 10 uL of Nextera were combined in a 2 mL tube with enzyme. The mixture was vortexed, spun, and placed on ice. 4 uL from elution plates was transferred to new PCR plates directly to the bottom without touching the walls. 1 uL of the buffer-enzyme mixture was transferred to the walls of the 96 well plates, which were then covered with transparent PCR film. A quick spin down was performed to start the reaction, and the plates were vortexed while holding a rubber seal on the top to prevent cross-contamination between wells, followed by a second quick spin. The plates were placed on a cycler with a constant temperature of 55° C. for about 5 minutes. The plates were removed from the cycler and DNA binding buffer was added to each well. The purification was repeated as described above and elution plates were used to which 1 uL of 25×PCR primer mix designed to incorporate a custom set of bar code sequences according to the manufacturer recommendations was added.

Example 11

PCR Reaction

Two plates were placed on ice and 12.5 uL of 2× Phusion GC polymerase master mix (NEB M0532L) was transfer to the plates. All of the volume eluted after the fragmentation reaction was transferred to the wells. The plates contain: 1 uL of 25×PCR primer mix that was added to elution plates; 11.5 uL of DNA eluted in water after Nextera step; and 12.5 uL of 2× Phusion polymerase. The plates were covered with transparent PCR film, vortexed, and spun. The plates were then placed on a cycler and thermocycled as shown in Table 3.

TABLE 3

| Step | Temperature | Time |
|---|---|---|
| 1 | 72 | 3:00 |
| 2 | 95 | 0:30 |
| 3 | 95 | 0:10 |
| 4 | 62 | 0:30 |
| 5 | 72 | 3:00 |
| 6 | Cycle to 4 for 8 more times | |
| 7 | 4 | hold |

Example 12

DNA Purification

The amplified DNA was purified using the Quiagen 96-well plate vacuum protocol, which is commercially available from Qiagen. 80 uL of PM (DNA binding buffer for Qiagen 96WP purification kit) was added to each well. Well contents were mixed and the volume from all 192 wells was transferred to 25 ml tray. The contents of the tray were transferred to 50 mL tubes and vortexed. The contents were then transferred to 16 wells of 96 well plate purification system and placed on vacuum manifold. The vacuum is turned on and left running until the liquid is gone. 900 uL of PE buffer was added to each well, and the vacuum again was turned on until the liquid was gone. 900 uL of PE buffer was added again to each well and the vacuum again was turned on for 10 minutes. 60 uL of TE was added to the center of each well and let sit for 2 minutes, and the vacuum again was turned on for 5 minutes. All contents were transferred to a single 2 mL tube.

Example 13

Size Selection

The nucleic acid was then size selected using Egel Syber safe (2% agarose) gels. The gels were pre-run gel for 2 minutes. 8 middle lanes of the gels were loaded with 16 uL of the purified sample from last step, the next two lanes were filled with clean water, 16 uL of 30 ng/uL ladder was added to the nearby wells. The gels were run for 30 minutes, opened, and the band from 500-700 bp was cut from the gels. The DNA was purified using two Qiaquick columns and eluted in 35 uL of TE.

The purified DNA is then run again. Another 2% sybr safe gel was pre-run for 2 minutes. 4 lanes with purified sample from the first gel purification were loaded, water was loaded in nearby wells and two ladder wells. Gels were run for 30 minutes, opened, and the band from 500-700 bp was cut. The DNA was purified using two Qiaquick columns and eluted in 35 uL of TE.

Example 14

Quantitation

Quantitation (i.e., estimating number of molecules that can form clusters on Illumina flowcell) was performed with qPCR relative to a know standard previously characterized by direct DNA sequencing, using Agilent bioanalyzer, or using Fluidigm digital PCR to get absolute library quantitation.

Example 15

Bioinformatic Pipeline

After reads were obtained from sequencing instrument, they were subjected to a number of quality checks. First, sequences similar to the Nextera insertion sequences were detected and removed from ends of the reads. This situation may happen if distance between two read primers is less than read length, for example due to imperfect final gel purification. Second, quality trimming was then performed to remove ends of the reads that has quality less than a certain threshold, in this protocol, less than 15. Third, overlaps were detected between paired reads, if detected reads were combined in one single read and stored in a separate single read pool.

Reads were then split by bar code by matching indexing reads to a set of 192 7 bp bar codes. Bar codes were designed such that they were at least two sequencing errors away from each other which makes miscalls very unlikely. High quality reads resulting from this process were then mapped to a genome reference in order to perform haplotype-resolved variant calling and obtain basic quality statistics.

Another pipeline used high quality reads for de-novo fragment assembly. Reads with certain bar codes were first preprocessed to correct low frequency kmers that were a result of sequencing errors. Resulting read pools were assembled in contigs, paired end read information was then used to combine contigs in scaffolds and partially mapped reads were then used to fill gaps in scaffolds. Resulting scaffolds were then assembled into bigger scaffolds using de-novo assemblers designed to work with Sanger data to produce draft genome assembly.

What is claimed is:

1. A method for obtaining a sequence, the method comprising:
   ligating adapters to a plurality of nucleic acid fragments in a sample, each nucleic acid fragment having a length between 5 kilobases and 40 kilobases;
   quantifying the amount of nucleic acid fragments present in the sample to which adapters have been ligated on each end, thereby quantifying the amount of amplifiable nucleic acid fragments;
   determining a dilution factor based on the quantified amount of amplifiable nucleic acid fragments;
   partitioning the sample based on the dilution factor such that each partitioned portion comprises, on average, at least two amplifiable nucleic acid fragments that are a subset of unique sequences;
   performing a polymerase chain reaction on the partitioned nucleic acid fragments;
   sequencing the nucleic acid fragments to obtain sequence reads; and
   obtaining a sequence from the reads.

2. The method according to claim 1, wherein prior to the ligating step, the method further comprises fragmenting nucleic acid.

3. The method according to claim 2, wherein the adapters comprise unique marker identifiers.

4. The method according to claim 3, wherein the unique marker identifiers comprise bar code sequences that are part of adapter sequences.

5. The method according to claim 4, wherein the bar code sequences in the adapters attached to both ends of a fragment are the same or different.

6. The method according to claim 4, wherein the adapter sequences are amplification adapters.

7. The method according to claim 3, further comprising attaching labels to the nucleic acid fragments in each partitioned portion.

8. The method according to claim 7, wherein the attaching labels step is performed after the polymerase chain reaction.

9. The method according to claim 8, wherein after the polymerase chain reaction, the method further comprises fragmenting the amplified nucleic acids in each partitioned portion.

10. The method according to claim 1, wherein partitioning comprises dispensing the sample into different wells of a microwell plate.

11. The method according to claim 1, wherein partitioning comprises segmenting the sample into droplets.

12. The method according to claim 1, wherein the sequence is a consensus sequence or a haplotype sequence.

13. A method for obtaining a sequence, the method comprising:

obtaining nucleic acid;

fragmenting the nucleic acid, thereby generating nucleic acid fragments that have a length of 5 kilobases to 40 kilobases;

ligating adapters to a portion of the nucleic acid fragments, wherein the portion of nucleic acid fragments with adapters ligated at each end are amplifiable nucleic acid fragments;

quantifying an amount of the amplifiable nucleic acid fragments present in the sample;

determining a dilution factor based on the quantified amount of amplifiable nucleic acid fragments;

partitioning the nucleic acid fragments based on the dilution factor, wherein each partitioned portion comprises, on average, at least two amplifiable nucleic acid fragments that are a subset of unique sequences;

amplifying the partitioned nucleic acid fragments by performing a polymerase chain reaction;

attaching bar codes to the amplified nucleic acid fragments;

sequencing the nucleic acid fragments to obtain bar coded sequence reads; and obtaining a sequence from the reads.

14. The method according to claim 13, wherein each adapter comprises a marker identifiers.

15. The method according to claim 13, wherein partitioning comprises dispensing the sample into different wells of a microwell plate.

16. The method according to claim 13, wherein partitioning comprises segmenting the sample into droplets.

17. The method according to claim 13, wherein the sequence is a consensus sequence or a haplotype sequence.

* * * * *